United States Patent
Lai et al.

(10) Patent No.: US 6,838,243 B2
(45) Date of Patent: Jan. 4, 2005

(54) METHODS AND COMPOSITIONS FOR POLYNUCLEOTIDE ANALYSIS USING GENERIC CAPTURE SEQUENCES

(75) Inventors: Jennifer H. Lai, Mountain View, CA (US); Vincent E. Phillips, Sunnyvale, CA (US); Andrew R. Watson, Belmont, CA (US)

(73) Assignee: Quantum Dot Corporation, Hayward, CA (US)

( * ) Notice: Subject to any disclaimer, the term of this patent is extended or adjusted under 35 U.S.C. 154(b) by 0 days.

(21) Appl. No.: 09/846,430

(22) Filed: Apr. 30, 2001

(65) Prior Publication Data

US 2003/0049620 A1 Mar. 13, 2003

Related U.S. Application Data

(60) Provisional application No. 60/200,635, filed on Apr. 28, 2000.

(51) Int. Cl.$^7$ .................... C12Q 1/68; C12P 19/34; C12M 1/34; C07H 21/02; C07H 21/04
(52) U.S. Cl. .................... 435/6; 435/7.1; 435/91.1; 435/91.2; 435/287.2; 536/22.1; 536/23.1; 536/24.3; 536/24.31; 536/24.32; 536/24.33
(58) Field of Search .................... 435/6, 7.1, 91.1, 435/91.2, 287.2; 536/22.1, 23.1, 24.3–24.33

(56) References Cited

U.S. PATENT DOCUMENTS

| | | | |
|---|---|---|---|
| 5,942,394 A | * 8/1999 | Ellis et al. .................... 435/6 |
| 5,990,479 A | 11/1999 | Weiss et al. | |
| 6,083,763 A | 7/2000 | Balch | |
| 6,207,392 B1 | 3/2001 | Weiss et al. | |
| 6,274,323 B1 | * 8/2001 | Bruchez et al. ................ 435/6 |
| 6,287,778 B1 | 9/2001 | Huang et al. | |
| 6,316,198 B1 | * 11/2001 | Skouv et al. .................. 435/6 |
| 6,426,197 B1 | * 7/2002 | Duckworth et al. ....... 435/69.1 |

OTHER PUBLICATIONS

Brenner et al., "Gene Expression Analysis by Massively Parallel Signature Sequencing (MPSS) on Microbead Arrays," *Nature Biotechnology* 18:630–634 (2000).

Chen et al., "A Microsphere–Based Assay for Multiplexed Single Nucleotide Polymorphism Analysis Using Single Base Chain Extension," *Genome Research* 10:549–557 (2000).

(List continued on next page.)

*Primary Examiner*—Jeffrey Siew
*Assistant Examiner*—Tracey D. Johnson
(74) *Attorney, Agent, or Firm*—Robins & Pasternak LLP

(57) ABSTRACT

Methods, compositions and articles of manufacture for assaying a sample for an amplification product from a target polynucleotide are provided. An amplification reaction is used to produce the amplification product from the target polynucleotide so that it can be used to indirectly assay the sample for the target polynucleotide. A sample suspected of containing the target polynucleotide is contacted with first and second primers to amplify the target polynucleotide; the first primer comprises a tag sequence, the complement of which is formed on the opposite strand during amplification and is referred to as a capture sequence. That opposite strand is referred to as a second primer extension product or an amplification product, and comprises a label. A capture probe is provided that is conjugated to a substrate and can bind to the capture sequence to form an amplification product detection complex. Methods of detecting the amplification product thus produced are also provided, as are amplification product assay arrays, along with methods of forming the same. The methods are particularly useful in multiplex settings where a plurality of target polynucleotides are to be assayed. Kits comprising reagents for performing such methods are also provided.

29 Claims, 15 Drawing Sheets

OTHER PUBLICATIONS

Favis et al., "Universal DNA Array Detection of Small Insertions and Deletions in *BRCA1* and *BRCA2*," *Nature Biotechnology* 18:561–564 (2000).

Gerry et al., "Universal DNA Microarray Method for Multiplex Detection of Low Abundance Point Mutations," *J. Mol. Biol.* 292:251–262 (1991).

Iannone et al., "Multiplexed Single Nucleotide Polymorphism Genotyping by Oligonucleotide Ligation and Flow Cytometry," *Cytometry* 39:139–140 (2000).

Myakishev et al., "High–Throughput SNP Genotyping by Alele–Specific PCR with Universal Energy–Transfer–Labeled Primers," *Genome Research* 11:163–169 (2001).

Tillib and Mirzabekov, "Advances in the Analysis of DNA Sequence Variations Using Oligonucleotide Microchip Technology," *Analytical Biotechnology* 12:53–58 (2001).

* cited by examiner

SEQUENCE LISTING

```
<160> NUMBER OF SEQ ID NOS: 5

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: LDLrA-GC1s

<400> SEQUENCE: 1
gcaataggtt ttgagggca tggttgtgga agaggac                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: LDLrB-GC1a

<400> SEQUENCE: 2
ttctgggcca ctgactgatt tggttgtgga agagaac                             37

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: LDLrab

<400> SEQUENCE: 3
ttcagtgcca accgcctcac                                                20

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: GC1s-A

<400> SEQUENCE: 4
tttttttttt ttttttttgc aataggtttt gaggggcat                           39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: GC1a-B

<400> SEQUENCE: 5
tttttttttt tttttttttt ctgggccact gactgattt                           39
```

METHODS AND COMPOSITIONS FOR POLYNUCLEOTIDE ANALYSIS USING GENERIC CAPTURE SEQUENCES

CROSS-REFERENCE TO RELATED APPLICATIONS

This application claims the benefit of priority to U.S. Provisional Patent Application No. 60/200,635, filed Apr. 28, 2000.

TECHNICAL FIELD

This invention relates to methods, articles and compositions for the analysis of polynucleotides in a sample.

BACKGROUND OF THE INVENTION

Michael Adams-Conroy died at the age of nine of the highest overdose of Prozac® on record, seven times higher than any previously known. His parents were investigated for homicide and his two siblings were removed from their custody by social welfare workers. Autopsy results, however, showed no pills in his stomach even though he would normally have had to ingest a huge number in order to reach the levels of drug found in his blood.

Acute lymphocytic leukemia (ALL) affects thousands of children each year in the United States. Treatment with chemotherapeutic agents now leads to remission in over 90% of the cases. 6-mercaptopurine (6-MP) is one agent used to treat ALL. However, the normal treatment dose of 6-MP is toxic for one in 300 patients and can kill rather than cure.

Adverse reactions to therapeutic drugs have been estimated to kill over 100,000 hospitalized patients in the U.S. each year (Lazarou et al., JAMA 4 1998 Apr. 15;279(15): 1200-5). This figure does not include intentional overdoses leading to hospitalization which ultimately prove fatal. An additional 2.2 million serious nonfatal adverse drug reactions have been estimated to occur.

The problem of the varied responses of individual patients to particular drug therapies is well known, but little progress has been made towards anticipating patients' varied drug metabolisms prior to treatment. The standard approach in administering drugs has been to prescribe the recommended dosage for a given condition to an affected patient, in some cases adjusting for the patient's weight. If the patient does not improve, the dosage is increased or an alternative drug is tried. Conversely, if adverse side effects occur, the dosage may be lowered or an alternative drug employed.

Drugs which exhibit serious side effects may never be approved by regulatory authorities or, if approved before such side effects are identified, can be withdrawn from the market if even a small percentage of treated patients are so affected. This can occur despite the fact that such drugs may have great therapeutic benefit in the majority of patients.

The 6-MP sensitivity exhibited by rare ALL patients has been linked to a deficiency in thiopurine S-methyltransferase (TPMT) activity (Krynetski et al., Pharm Res 1999 16(3): 342–9). Patients deficient in this enzyme can be treated with lower doses of 6-MP to achieve the same therapeutic plasma levels while avoiding adverse toxicity if the prescribing physician is aware of the metabolic deficiency. Metabolism of similar drugs such as azathioprine and thioguanine used in the treatment of rheumatoid arthritis, leukemia and Crohn's disease is also affected in patients who are deficient in TPMT.

Cytochrome p-450 CYP2D6 (debrisoquin hydroxylase) is the primary enzyme responsible for human metabolism of fluoxetine (Prozac®), as well as codeine, amphetamines, methadone, and several antidepressants and neuroleptics. At least twenty variants of the CYP2D6 gene are now known to result in poor metabolism of Prozac® and other drugs (Wong et al., Ann Acad Med Singapore 2000 29(3):401–6). Approximately 7–10% of Caucasians are poor metabolizers of Prozac®, and reach higher than expected plasma levels when treated with a standard dosage.

Michael Adams-Conroy was one such patient, but he was never tested to determine whether he harbored any of the CYP2D6 variants resulting in slow metabolism of Prozac. Instead, because of his diminished response to Prozac®, as typically occurs with chronic use, his dosage was gradually increased to maintain control over his symptoms. Side effects associated with Prozac® toxicity such as nausea and dizziness were instead attributed to migraines. Only after Michael's death were his tissues tested and shown to contain CYP2D6 variants which contributed to a toxic accumulation of Prozac® and its metabolites in his blood (Sallee et al., J. Child Adolesc. Psychopharmacol. 2000 Spring; 10(1): 27–34).

Potentially fatal adverse drug reactions are now known to be associated with altered metabolism by patients harboring variants in a number of genes, including in the NA12 gene affecting isoniazid metabolism, in the CYP2C9 gene affecting warfarin metabolism, in the DPD gene affecting 5-fluorouracil metabolism, and in the KCNE2 gene affecting clarithromycin metabolism (Grant et al., Pharmacology 2000 61(3):204–11; Taube et al., Blood 2000 96(5):1816–9; Meinsma et al., DNA Cell Bio 1995 14(1):1–6; Sesti et al., Proc Natl Acad Sci USA 2000 97(19):10613–8).

There is a need in the art for methods of analyzing samples for particular polynucleotides, and for devices, compositions and articles of manufacture useful in such methods.

SUMMARY OF THE INVENTION

Methods, compositions and articles for assaying a sample for an amplification product from a target polynucleotide are provided. In one aspect, a method is provided comprising contacting a sample suspected of containing the amplification product with a first capture probe conjugated to a substrate. The substrate can be a spectrally encoded microsphere. Amplification reactions can be incorporated into the methods.

The capture probe binds to a capture sequence which does not normally occur in the amplification product produced from the target polynucleotide. The capture sequence is introduced into the amplification product via primer-mediated extension from a template. A first primer is used to prime the synthesis of a complementary strand to the target polynucleotide, forming a first primer extension product ("PEP"). The first primer comprises a target complementary region ("target CR" or "TCR") at its 3' end which is complementary to the target polynucleotide, and introduces a target noncomplementary region ("target NCR" or "TNCR") into the first PEP that does not normally occur adjacent to the target CR in a complementary strand to the target polynucleotide. A second primer is used to prime synthesis from the first PEP to form a second PEP, also called the amplification product. The second PEP comprises a label and a sequence that is complementary to the target noncomplementary region in the first primer; this complementary sequence is referred to as the capture sequence. The capture sequence binds to the capture probe to localize the second PEP to the substrate, forming an amplification product detection complex. Identification of the label in association with the substrate demonstrates that the amplification product was formed and the target polynucleotide was present in the sample.

Binding of the capture sequence to the capture probe results in the formation of an amplification detection assay complex. Where a plurality of different capture probes are attached to the same substrate, binding of a plurality of corresponding different labeled amplification products results in the formation of an amplification product assay array.

Kits comprising reagents useful for performing the methods of the invention are also provided.

The methods are particularly useful in multiplex settings where a plurality of different capture probes are used to assay for a plurality of different target polynucleotides. The large number of distinguishable semiconductor nanocrystal labels can be employed to simultaneously analyze differently labeled target polynucleotides and/or different spectrally encoded beads.

Methods of the invention can optionally be implemented in a homogeneous format. This allows for higher assay throughput due to fewer manipulations of the sample, and decreased cross-contamination resulting in more reliable assays and less downtime from cross-contamination. If real time monitoring is used, the entire assay can be disposed of without opening a sealed assay chamber such as a sealed microplate, thus further decreasing the risk of cross-contamination.

DETAILED DESCRIPTION OF THE INVENTION

Figure 1:
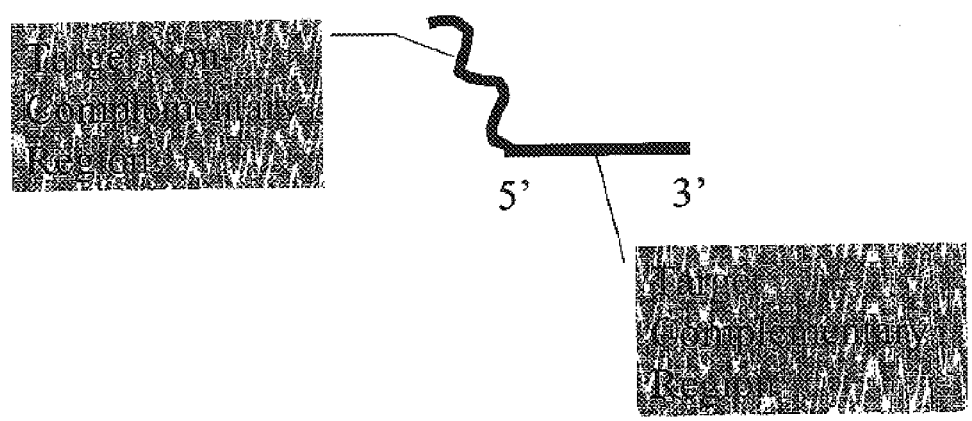
FIG. 1 depicts a first primer comprising a 5' end, a 3' end, a target noncomplementary region, and a target complementary region at the 3' end.

Gene variants are not only associated with adverse drug side effects. Variations in genes controlling patient drug response can also correlate with the inability of drugs to result in a successful therapeutic outcome. For example, Alzheimer's patients having the ApoE E4 subtype are less likely to benefit from the drug tacrine PNAS 1995, 92:12260–4, Poirier et al.).

Inventions useful for assaying for particular polynucleotide sequences, whether based on SNPs, conserved sequences, or other features, have use in a wide variety of different applications. In addition to pharmacogenetic testing, such methods can be used in a forensic setting to identify the species or individual which was the source of a forensic specimen. Polynucleotide analysis methods can also be used in an anthropological setting. Paternity testing is another area in which the invention can be used, as is testing for compatibility between prospective tissue or blood donors and patients in need thereof, and in screening for hereditary disorders.

The invention taught herein can be used to study alterations of gene expression in response to a stimulus. Other applications include human population genetics, analyses of human evolutionary history, and characterization of human haplotype diversity.

The invention can also be used: to detect immunoglobulin class switching and hypervariable mutation of immunoglobulins; to detect polynucleotide sequences from contaminants or pathogens including bacteria, yeast and viruses; for HIV subtyping to determine the particular strains or relative amounts of particular strains infecting an individual; and can be done repeatedly to monitor changes in the individuals predominant HIV strains, such as the development of drug resistance or T cell tropism; and to detect single nucleotide polymorphisms, which may be associated with particular alleles or subsets of alleles. Over 1.4 million different single nucleotide polymorphisms (SNPs) in the human population have been identified (Nature 2001 409:928–933).

The invention can be used for mini-sequencing, and for detection of mutations. Any type of mutation can be detected, including without limitation SNPs, insertions, deletions, transitions, transversions, inversions, frame shifts, triplet repeat expansions, and chromosome rearrangements. The invention can be used to detect nucleotide sequences associated with increased risk of diseases or disorders, including cystic fibrosis, Tay-Sachs, sickle-cell anemia, etc.

The invention described herein are useful for any assay in which a sample can be interrogated regarding an amplification product from a target polynucleotide. Typical assays involve determining the presence of the amplification product in the sample or its relative amount, or the assays may be quantitative or semiquantitative. Results from such assays can be used to determine the presence or amount of the target polynucleotide originally present in the sample.

A sample suspected of containing the amplification product is contacted with a first capture probe conjugated to a substrate. The capture probe binds to a capture sequence which does not naturally occur in the amplification product. The capture sequence is introduced into the amplification product via primer-mediated extension from a template. Amplification reactions used to form the amplification product are also within the scope of the invention. A first primer is used to prime the synthesis of a complementary strand to the target polynucleotide, forming a first primer extension product. The first primer comprises a target complementary region at its 3' end and a target noncomplementary region. A second primer is used to prime polynucleotide synthesis from the first PEP to form the second PEP, also referred to as the amplification product. The second PEP comprises a label and a sequence that is complementary to the target noncomplementary region in the first primer; this complementary sequence is referred to as the capture sequence. The label can be incorporated into the second PEP by any means, including by incorporation of labeled nucleotides during extension from the second primer, but preferably the second primer itself comprises the label to increase specificity. The capture sequence binds to the capture probe to localize the second PEP to the substrate, forming an amplification product detection complex. Identification of the label in association with the substrate demonstrates that the amplification product was formed and the target polynucleotide was present in the sample.

The capture probe can be any material which can bind to the capture sequence in the second primer extension product. The capture probe can be linked directly or indirectly to the substrate. The capture probe typically is a polynucleotide, and can be linked to the substrate at any point in the polynucleotide which allows its use under assay conditions. The capture probe may also bind to additional sequence in the second primer extension product beyond the capture sequence, so long as it does not bind to any polynucleotide lacking the capture sequence to a degree that prevents its use in the assay to be performed.

The methods of the invention can all be performed in multiplex formats. A plurality of different capture probes which preferentially bind to corresponding different capture sequences in amplification products can be conjugated to the same substrate, or to a plurality of different distinguishable substrates. The separate binding of each different capture sequence to its corresponding capture probe can be detected by incorporating a different label on each different amplification product, by the location on the substrate at which each capture probe is located, by the conditions under which each capture sequence binds, or combinations thereof Multiplex methods are provided employing 2, 3, 4, 5, 10, 15, 20, 25, 50, 100, 200, 500, 1000 or more different capture probes which can be used simultaneously to assay for amplification products from corresponding different target polynucleotides.

Methods amenable to multiplexing, such as those taught herein, allow acquisition of greater amounts of information from smaller specimens. The need for smaller specimens increases the ability of an investigator to obtain samples from a larger number of individuals in a population to validate a new assay or simply to acquire data, as less invasive techniques are needed.

Where different substrates are included in a multiplex assay, the different substrates can be encoded so that they can be distinguished. Any encoding scheme can be used; conveniently, the encoding scheme can employ one or more different fluorophores, which can be fluorescent semiconductor nanocrystals. High density spectral coding schemes can be used.

One or more different populations of spectrally encoded bead conjugates can be created, each population comprising one or more different capture probes attached to a microsphere comprising a known or determinable spectral code comprising one or more semiconductor nanocrystals. Different populations of the conjugates, and thus different assays, can be blended together, and the assay can be performed in the presence of the blended populations. The individual conjugates are scanned for their spectral properties, which allows the spectral code to be decoded and thus identifies the bead, and therefore the capture probe(s) to which it is attached. Because of the large number of different semiconductor nanocrystals and combinations thereof which can be distinguished, large numbers of different capture probes and amplification products can be simultaneously interrogated.

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target polynucleotide" includes a plurality of target polynucleotides, reference to "a substrate" includes a plurality of such substrates, reference to "a capture probe" includes a plurality of capture probes, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

The terms "semiconductor nanocrystal," "SCNC," "quantum dot" and "Qdot™ nanocrystal" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). SCNCs are characterized by their uniform nanometer size. An SCNC is capable of emitting electromagnetic radiation upon excitation (i.e., the SCNC is luminescent) and includes a "core" of one or more first semiconductor materials, which may be surrounded by a "shell" of a second semiconductor material. An SCNC core surrounded by a semiconductor shell is referred to as a "core/shell" SCNC. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, Pb, PbS, PbSe, and an alloy or a mixture thereof. Preferred shell materials include CdS and ZnS.

An SCNC is optionally surrounded by a "coat" of an organic capping agent. The organic capping agent may be any number of materials, but has an affinity for the SCNC surface. In general, the capping agent can be an isolated organic molecule, a polymer (or a monomer for a polymerization reaction), an inorganic complex, or an extended crystalline structure. The coat can be used to convey solubility, e.g., the ability to disperse a' coated SCNC homogeneously into a chosen solvent, functionality, binding properties, or the like. In addition, the coat can be used to tailor the optical properties of the SCNC.

Thus, the terms "semiconductor nanocrystal," "SCNC," "quantum dot" and "Qdot™ nanocrystal" as used herein include a coated SCNC core, as well as a core/shell SCNC.

"Monodisperse particles" include a population of particles wherein at least about 60% of the particles in the population, more preferably about 75 to about 90, or any integer therebetween, percent of the particles in the population fall within a specified particle size range. A population of monodisperse particles deviates less than 10% rms (root-mean-square) in diameter, and preferably deviates less than 5% rms.

The phrase "one or more sizes of SCNCs" is used synonymously with the phrase "one or more particle size distributions of SCNCs." One of ordinary skill in the art will realize that particular sizes of SCNCs are actually obtained as particle size distributions.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyanide (e.g., peptide nucleic acids ("PNAs")) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'-H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine may be prepared by the method described by Switzer et al. (1993) Biochemistry 32:10489–10496 and references cited therein; 2'-deoxy-5-methyl-isocytidine may be prepared by the method of Tor et al. (1993) J. Am. Chem. Soc. 115:4461–4467 and references cited therein; and isoguanine nucleotides may be prepared using the method described by Switzer et al. (1993), supra, and Mantsch et al. (1993) Biochem. 14:5593–5601, or by the method described in U.S. Pat. No. 5,780,610 to Collins et al. Other nonnatural base pairs may be synthesized by the method described in Piccirilli et al. (1990) Nature 343:33–37 for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al. (1992) J. Am. Chem. Soc. 114:3675–3683 and Switzer et al., supra.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

"Complementary" or "substantially complementary" refers to the ability to hybridize or base pair between nucleotides or nucleic acids, such as, for instance, between the two stands of a double stranded DNA molecule or between a polynucleotide primer and a primer binding site on a single stranded nucleic acid to be sequenced or amplified. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide or capture probe to bind to a complementary target polynucleotide in a sample as compared to noncomplementary polynucleotides in the sample or as compared to the propensity of the one polynucleotide to form an internal secondary structure such as a hairpin or stem-loop structure under at least one set of hybridization conditions.

Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art. Less stringent, and/or more physiological, hybridization conditions are used where a labeled polynucleotide amplification product cycles on and off a substrate linked to a capture probe during a real-time assay which is monitored during PCR amplification such as a molecular beacon assay. Such less stringent hybridization conditions can also comprise solution conditions effective for other aspects of the method, for example reverse transcription or PCR.

The terms "aptamer" (or "nucleic acid antibody") is used herein to refer to a single- or double-stranded polynucleotide that recognizes and binds to a desired target molecule by virtue of its shape. See, e.g., PCT Publication Nos. WO 92/14843, WO 91/19813, and WO 92/05285.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides contain co- and/or post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

The terms "substrate" and "support" are used interchangeably and refer to a material having a rigid or semi-rigid surface.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

An "SCNC conjugate" is an SCNC linked to a first member of a binding pair, as defined above. For example, an SCNC is "linked" or "conjugated" to, or chemically "associated" with, a polynucleotide when the SCNC is coupled to, or physically associated with the polynucleotide. Thus, these terms intend that the SCNC may either be directly linked to the polynucleotide or may be linked via a linker moiety, such as via a chemical linker. The terms indicate items that are physically linked by, for example, covalent chemical bonds, physical forces such van der Waals or hydrophobic interactions, encapsulation, embedding, or the like. For example, nanocrystals can be associated with biotin which can bind to the proteins avidin and streptavidin.

The term "antibody" as used herein includes antibodies obtained from both polyclonal and monoclonal preparations, as well as: hybrid (chimeric) antibody molecules (see, for example, Winter et al. (1991) *Nature* 349:293–299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B:120–126); humanized antibody molecules (see, for example, Riechmann et al. (1988) *Nature* 332:323–327; Verhoeyan et al. (1988) *Science* 239:15341536; and U.K. Patent Publication No. GB 2,276, 169, published 21 September 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. *Monoclonal Antibodies and Cancer Therapy*, Alan R. Liss, 1985, p. 77.

A "homogeneous assay" is one that is performed without taansfer, separation or washing steps. Thus, for example, a homogeneous high-throughput screening ("HTS") assay involves the initial addition of reagents to a vessel, e.g., a test tube or sample well, followed by the detection of the results from that vessel. A homogeneous HTS assay can be performed anywhere in the vessel, for example in the solution, on the surface of the vessel or on beads or surfaces placed in the vessel. The detection system typically used is a fluorescence, chemiluminescence, or scintillation detection system.

"Multiplexing" herein refers to an assay or other analytical method in which multiple probe polynucleotides can be assayed simultaneously by using more than one SCNC, each of which has at least one different fluorescence characteristic (for example excitation wavelength, emission wavelength, emission intensity, FWHM (full width at half maximum peak height), or fluorescence lifetime). Multiplexing also includes assays or methods in which the combination of more than one SCNC having distinct emission spectra can be used to detect a single probe polynucleotide.

For example, two different preparations of SCNCs may have the same composition but different particle sizes, and thus differ in excitation and/or emission wavelength. Or, two different preparations may have the same particle size or particle size distribution but different composition, and thus also differ in excitation and/or emission wavelength. Different preparations having different compositions of SCNCs can have different fluorescent lifetimes, and thus their emission spectra can be distinguished even when they have the same emission wavelength and intensity, for example by sampling the emission from the encoded substance at different times after excitation. Differences in FWHM can be achieved for example by using SCNCs of different composition, or of the same composition but which are synthesized differently, or by mixing different SCNC "preparations" having overlapping emission peaks together to form a new preparation.

A SCNC having a known emission wavelength and/or intensity may be included with the SCNCs conjugated to the polynucleotide defined herein to provide an internal standard for calibrating the wavelength and/or intensity of the other SCNC(s) used in the conjugate.

"Optional" or "optionally" means that the subsequently described event or circumstance may or may not occur, and that the description includes instances where the event or circumstance occurs and instances in which it does not. For example, the phrase "optionally surrounded by a 'coat' of an organic capping agent" with reference to an SCNC includes SCNCs having such a coat, and SCNCs lacking such a coat.

The Sample

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample can also comprise a target polynucleotide prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant source, e.g. a library, comprising polynucleotide sequences.

The sample can be a positive control sample which is known to contain the target polynucleotide or a surrogate therefor. A negative control sample can also be used which, although not expected to contain the target polynucleotide, is suspected of containing it, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

The Target Polynucleotide and Amplification Products Produced Therefrom

The target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide prior to amplification. Conversely, where the target polynucleotide is too concentrated for a particular assay, the target polynucleotide may first be diluted.

Following sample collection and optional nucleic acid extraction and purification, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer, which can be the first primer comprising the target noncomplementary regtion, to create cDNA prior to detection and/or further amplification; this can be done in vitro with purified mRNA or in situ, e.g. in cells or tissues affixed to a slide. Nucleic acid amplification increases the copy number of sequences of interest and can be used to incorporate a label into an amplification product produced from the target polynucleotide using a labeled primer or labeled nucleotide. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like, particularly where a labeled amplification product can be produced and utilized in the methods taught herein.

Where the target polynucleotide is single-stranded, the first cycle of amplification forms a primer extension product complementary to the target polynucleotide. If the target polynucleotide is single-stranded RNA, a polymerase with reverse transcriptase is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to prime the synthesis of the complementary template strand.

The target polynucleotide is typically amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity. The polymerase can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and Pyrococcus sp GB-D DNA polymerases; RNA polymerases such as *E. coli*, SP6, T3 and T7 RNA polymerases; and reverse transcriptases such as AMV, M-MULV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and Pyrococcus sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions, optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifgal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different regions of a particular polynucleotide within the sample.

Where the amplification reaction comprises multiple cycles of amplification with a polymerase, as in PCR, it is desirable to dissociate the primer extension product(s) formed in a given cycle from their template(s). The reaction conditions are therefore altered between cycles to favor such dissociation; typically this is done by elevating the temperature of the reaction mixture, but other reaction conditions can be altered to favor dissociation, for example lowering the salt concentration and/or raising the pH of the solution in which the double-stranded polynucleotide is dissolved. Although it is preferable to perform the dissociation in the amplification reaction mixture, the polynucleotides may be first isolated using any effective technique and transferred to a different solution for dissociation, then reintroduced into an amplification reaction mixture for additional amplification cycles.

In one aspect of the invention, first and second primers are used to amplify a specific target polynucleotide. A first primer is provided comprising at its 3' end a target complementary region that is complementary to a predetermined target polynucleotide, and a target noncomplementary region, typically at its 5' end. The target noncomplementary region is preferably introduced into the fist primer during synthesis, but could also be introduced via ligation. The target NCR can be designed so that its complement is an aptamer designed to bind specifically to the capture probe. The target NCR preferably has a unique sequence that is not expected to occur in the sample, but at a minimum must be a sequence which is not complementary to the sequence in the target polynucleotide which is 3' of the sequence to which the target CR binds, and also must not otherwise occur in the amplification product produced by the amplification scheme employed. Hybridization of the first primer to the target polynucleotide and extension results in formation of a first primer extension product.

A second, or "reverse," primer is provided that is complementary to a sequence in the first primer extension product which is 3' from the 3' end of the first primer. This second primer will anneal to the first primer extension product and can be extended in the opposite direction to form the second primer extension product. This second PEP comprises a capture sequence that is complementary to the target NCR in the first PEP. A label must be incorporated into the second PEP in order for it to be detected when bound to the capture probe. Preferably this is done by incorporation of a label into the second primer, which would create an absolute requirement for both primers to produce a detectable second PEP. Label could also be incorporated by incorporating a labeled nucleotide during amplification, although this would not create an absolute requirement for the second PEP such that spurious priming by the first PEP alone in two directions could lead to a false positive result. Multiple cycles of such an amplification scheme can be performed. First PEPs produced in subsequent cycles from the first primer hybridizing to the second PEP and being extended may be shorter than first PEPs produced from the target polynucleotide where only a portion of the target polynucleotide is amplified.

It should be noted that "first" and "second" primer are relative terms. It is possible in some embodiments for the second primer to bind to a complement of the desired target polynucleotide, e.g. where the target polynucleotide is one strand of dsDNA. However, the only productive initiation of polynucleotide amplification occurs where the first primer binds and is extended to form the first PEP; a second PEP comprising the capture sequence is only formed by priming from that first PEP comprising the target noncomplementary region, i.e., from the second primer annealing to the first PEP at a position which is 3' to the 3' end of the first primer.

Where one allele or a subset of alleles of closely related sequences are to be selectively assayed, at least one of the first and second primers must be selective for that allele or subset of alleles. This is typically done by having the 3' end of one of the primers overlap, typically by at least one to five nucleotides, a sequence variation which is specific to that allele or subset. This overlap allows the selective primer to preferentially bind and/or be extended from its exact match, with little or no extension from other alleles which may be present in the sample. Where the sequence variation being assayed is minimal, such as a SNP, the selective primer may hybridize to incorrect alleles; in a multiplex setting designed to detect both alleles of a SNP, such hybridization to incorrect alleles may adversely affect production of amplification product from the correct allele, an effect which only increases during amplification as the correct primer is diminished, leaving relatively higher concentrations of the mismatched primer. This effect can be minimized in various ways, including, for example, by incorporating a flanking primer which is located upstream, or 5', from the selective primer in the target polynucleotide to increase the copy number of the template used for forming the first primer extension product. This flanking primer can have a lower melting temperature for binding to the target polynucleotide than the selective primer, so that the annealing temperature can be raised at some point during the amplification scheme to favor hybridization of the selective primer over the flanking primer.

This assay can be multiplexed, i.e., multiple distinct assays can be run simultaneously, by using different pairs of primers directed at different targets, which can be unrelated targets, or different alleles or subgroups of alleles from, or chromosomal rearrangements at, the same locus. This allows the quantitation of the presence of multiple target polynucleotides in a sample (e.g. specific genes in a cDNA library). All that is required is an ability to uniquely identify the different second polynucleotide extension products in such an assay, through either a unique capture sequence or a unique label.

Amplified target polynucleotides may be subjected to post-amplification treatments. For example, in some cases, it may be desirable to fragment the amplification products prior to hybridization with a polynucleotide array, in order to provide segments which are more readily accessible and which avoid looping and/or hybridization to multiple capture probes. Fragmentation of the nucleic acids can be carried out by any method producing fragments of a size useful in the assay being performed; suitable physical, chemical and enzymatic methods are known in the art.

The amplification reaction can also be subjected to post-amplification treatments which remove undesirable components of the reaction mixture prior to detection. For example, unincorporated primers may be removed which might inhibit binding of the amplification product to the capture probe (unincorporated first primers, which contain the target NCR, can hybridize to the capture sequence and compete for binding of the capture sequence in the amplification product). Unincorporated primers can be removed, for example, by adding a single-stranded DNA nuclease (or other nuclease having a specificity for one or more components of the first primer) which can digest the unincorporated primers at a point in the amplification scheme at which the first and second PEPs should be hybridized in double-stranded form if they are present. The nuclease is preferably thermolabile so that the mixture can be heated to inactivate the nuclease so that the first and second PEPs can be dissociated without their digestion before detection. Or the first primer may incorporate alternative bases which allow the first primer to be selectively destroyed; for example, the first primer may incorporate uracils which can be removed by digestion with uracil DNA glycosylase.

An amplification reaction can be performed under conditions which allow the capture probe to hybridize to the amplification product during at least part of an amplification cycle. When the assay is performed in this manner, real-time detection of this hybridization event can take place by monitoring for a change in fluorescence properties of the substrate that occurs upon such hybridization during the amplification. Alternatively, the amplification reaction may occur under conditions which do not allow such binding during cycling, for example elevated temperature or in the absence of the probe polynucleotide, and the condition of the sample must be altered to allow detection to take place, for example by lowering the temperature or by contacting the sample with the first or probe polynucleotide. The stem-loop structure described below can be designed with the amplification reaction conditions in mind to either hybridize during an amplification cycle or not.

The Capture Probe

A capture probe is provided that is conjugated to a substrate. The capture probe can be any material which can selectively bind to the capture sequence in the second primer extension product of interest without binding significantly to any other material in the amplified sample, and especially without binding significantly to any other labeled polynucleotide produced in the amplification reaction. The capture probe can be an antibody, an aptamer, a sequence specific binding moiety such as a transcription factor or zinc finger binding protein, a binding partner for the capture sequence, or a polynucleotide as defined above, including without limitation a peptide nucleic acid. Where the capture probe is a polynucleotide, it can be branched, multimeric or circular, but is typically linear, and can contain nonnatural bases designed to bind more tightly to the capture sequence than the target noncomplementary region in the first primer can.

Where the capture probe is a polynucleotide, it can be synthesized directly on the substrate, or can be synthesized separately from the substrate and then coupled to it. Direct synthesis on the substrate may be accomplished by incorporating a monomer that is coupled to a subunit of the capture probe into a polymer that makes up or is deposited on or coupled to the substrate, and then synthesizing the remainder of the capture probe to incorporate that subunit. Alternatively, the substrate or its coating may include or be derivatized to include a functional group which can be coupled to a subunit of the capture probe for synthesis, or may be coupled directly to the complete capture probe. Suitable coupling techniques are known in the art. The length of the capture probe polynucleotide is not critical, but typically is from 5–100 nucleotides in length and is chosen to provide suitably selective binding and capture of the intended second primer extension product. The sequence of the capture probe polynucleotide can be identical to the target noncomplementary region on the first PCR primer.

Hybridization of the second primer extension product to the capture probe conjugated to the substrate forms an amplification product assay complex. An amplification product assay array comprising a plurality of different capture probes conjugated to a substrate having different sequences hybridized to corresponding different labeled amplification products can also be prepared.

The Substrate

The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof.

Substrates can be planar crystalline substrates such as silica based substrates (e.g. glass, quartz, or the like), or crystalline substrates used in, e.g., the semiconductor and microprocessor industries, such as silicon, gallium arsenide and the like.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the substrate takes an inanimate form, for some applications such as flow cytometry or in situ hybridization, the substrate can be any form that is rigid or semi-rigid, for example a cell, tissue, organism or nucleus, and may be optionally fixed. The substrate may contain raised or depressed regions on which a capture probe is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

The substrate and/or its optional surface are chosen to provide appropriate optical characteristics for the synthetic and/or detection methods used. The substrate and/or surface can be transparent to allow the exposure of the substrate by light applied from multiple directions. The substrate and/or surface may be provided with reflective "mirror" structures to increase the recovery of light emitted by the semiconductor nanocrystal or other label. The substrate and/or its surface may also be coated to decrease the amount of spurious incident light.

The substrate and/or its surface is generally resistant to, or is treated to resist, the conditions to which it is to be exposed in use, and can be optionally treated to remove any resistant material after exposure to such conditions.

Targets can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767–777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCTUS93/04145 and pin based methods such as those described in U.S. Pat. No. 5,288,514.

Additional flow channel or spotting methods applicable to attachment of targets to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

A Microsphere Substrate

In a preferred embodiment, the substrate can be in the form of a microsphere. Polymeric microspheres or beads can be prepared from a variety of different polymers, including but not limited to polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nm to 1 mm, and can be manipulated using normal solution techniques when suspended in a solution. The terms "bead," "sphere," "microbead" and "microsphere" are used interchangeably herein.

A plurality of such beads or mixtures of different bead populations can be immobilized on a planar surface such that they are regularly spaced in a chosen geometry using any suitable method. For example, beads can be immobilized by micromachining wells in which beads can be entrapped into the surface, or by patterned activation of polymers on the surface using light activation to cross-link single beads at particular locations. Suitable wells can be created by ablating circles in a layer of parylene deposited on a glass surface using a focused laser. The well dimensions are chosen such that a single bead can be captured per well and remain trapped when a lateral flow of fluid passes across the surface. For example, 7 micron wells can be readily used for analysis of beads about 4 microns to about 6 microns in diameter. This can be performed on the end of an optical fiber.

Spectrall Encoded Microspheres

Microspheres can be spectrally encoded through incorporation of SCNCs. Conjugation of a capture probe to such an encoded microsphere produces an encoded bead conjugate. The desired fluorescence characteristics of the microspheres maybe obtained by mixing SCNCs of different sizes and/or compositions in a fixed amount and ratio to obtain the desired spectrun, which can be determined prior to association with the microspheres. Subsequent treatment of the microspheres (through for example covalent attachment, co-polymerization, or passive absorption or adsorption) with the staining solution results in a material having the designed fluorescence characteristics.

A number of SCNC solutions can be prepared, each having a distinct distribution of sizes and compositions, to achieve the desired fluorescence characteristics. These solutions may be mixed in fixed proportions to arrive at a spectrum having the predetermined ratios and intensities of emission from the distinct SCNCs suspended in that solution. Upon exposure of this solution to a light source, the emission spectrum can be measured by techniques that are well established in the art. If the spectrum is not the desired spectrum, then more of the SCNC solution needed to achieve the desired spectrum can be added and the solution "titrated" to have the correct emission spectrum. These solutions may be colloidal solutions of SCNCs dispersed in a solvent, or they may be pre-polymeric colloidal solutions, which can be polymerized to form a matrix with SCNCs contained within.

The composition of the staining solution can be adjusted to have the desired fluorescence characteristics, preferably under the exact excitation source that will be used for the decoding. A multichannel auto-pipettor connected to a feedback circuit can be used to prepare an SCNC solution having the desired spectral characteristics, as described above. If the several channels of the titrator/pipettor are charged with several unique solutions of SCNCs, each having a unique excitation and emission spectrum, then these can be combined stepwise through addition of stock solutions.

Once the staining solution has been prepared, it can be used to incorporate a unique spectral code into a given bead population. If the method of incorporation of the SCNCs into the beads is absorption or adsorption, then the solvent that is used for the staining solution should be one that is suitable for swelling the microspheres, and can be selected based on the microsphere composition. Typical solvents for swelling microspheres include those in which the microsphere material is more soluble, for example dichloromethane, chloroform, dimethylformamide, tetrahydrofuran and the like. These can be mixed with a solvent in which the microsphere material is less soluble, for example methanol or ethanol, to control the degree and rate of incorporation of the staining solution into the material.

The microspheres swell when added to the staining solution and incorporate a plurality of SCNCs in the relative proportions that are present in the staining solution. After removal of the staining solution from the material, a non-swelling solvent is added, the material shrinks, or unswells, thereby trapping the SCNCs in the material. Alternatively, SCNCs can be trapped by evaporation of the swelling solvent from the material. After rinsing with a nonswelling solvent in which the SCNCs can be suspended, the SCNCs are trapped in the material, and can be retained by further use of a nonswelling solvent. Typical nonswelling solvents include hexane and toluene. The thus-encoded beads can be separated and exposed to a variety of solvents without a change in the emission spectrum under the light source. When the material used is a polymer bead, the material can be separated from the rinsing solvent by any suitable technique, for example, centrifugation, evaporation, fluidized bed drying, etc., or combined procedures, and can be redispersed into aqueous solvents and buffers through the use of detergents in the suspending buffer.

The staining procedure can also be carried out in sequential steps. A first staining solution can be used to stain the beads with one population of SCNCs. The beads can then be separated from the first staining solution and added to a second staining solution to stain the beads with a second population of SCNCs. These steps can be repeated until the desired spectral properties are obtained from the material when excited by a light source.

The SCNCs can be attached to the beads by covalent attachment as well as by entrapment in swelled beads, or can be coupled to one member of a binding pair the other member of which is attached to the beads. For instance, SCNCs are prepared by a number of techniques that result in reactive groups on the surface of the SCNC. See, e.g., Bruchez et al. (1998) Science 281:2013–2016, Chan et al. (1998) Science 281:2016–2018, Colvin et al. (1992) J. Am. Chem. Soc. 114:5221–5230, Katari et al. (1994) J. Phys. Chem. 98:4109–4117, Steigerwald et al. (1987) J. Am. Chem. Soc. 110:3046. The reactive groups present on the surface of the SCNCs can be coupled to reactive groups present on a surface of the material. For example, SCNCs which have carboxylate groups present on their surface can be coupled to beads with amine groups using a carbodiimide activation step.

Any cross-linking method that links a SCNC to a bead and does not adversely affect the properties of the SCNC or the bead can be used. In a cross-linking approach, the relative amounts of the different SCNCs can be used to control the relative intensities, while the absolute intensities can be controlled by adjusting the reaction time to control the number of reacted sites in total. After the beads are crosslinked to the SCNCs, the beads are optionally rinsed to wash away unreacted SCNCs.

A sufficient amount of fluorophore must be used to encode the beads so that the intensity of the emission from the fluorophores can be detected by the detection system used and the different intensity levels must be distinguishable, where intensity is used in the coding scheme but the fluorescence emission from the SCNCs or other fluorophores used to encode the beads must not be so intense to as to saturate the detector used in the decoding scheme.

The Coding Scheme

The beads or other substrate to which one or more different known capture probes are conjugated can be encoded to allow rapid analysis of bead, and thus capture probe, identity, as well as allowing multiplexing. The coding scheme preferably employs one or more different SCNCs, although a variety of additional agents, including chromophores, fluorophores and dyes, and combinations thereof can be used alternatively or in combination with SCNCs. For organic dyes, different dyes that have distinguishable fluorescence characteristics can be used. Different SCNC populations having the same peak emission wavelength but different peak widths can be used to create different codes if sufficient spectral data can be gathered to allow the populations to be distinguished. Such different populations can also be mixed to create intermediate linewidths and hence more unique codes.

The number of SCNCs used to encode a single bead or substrate locale can be selected based on the particular application. Single SCNCs can be detected; however, a plurality of SCNCs from a given population is preferably incorporated in a single bead to provide a stronger, more continuous emission signal from each bead and thus allow shorter analysis time.

Different SCNC populations can be prepared with peak wavelengths separated by approximately 1 nm, and the peak wavelength of an individual SCNC can be readily determined with 1 nm accuracy. In the case of a single-peak spectral code, each wavelength is a different code. For example, CdSe SCNCs have a range of emission wavelengths of approximately 490–640 nm and thus can be used to generate about 150 single-peak codes at 1 nm resolution.

A spectral coding system that uses only highly separated spectral peaks having minimal spectral overlap and does not require stringent intensity regulation within the peaks allows for approximately 100,000 to 10,000,000 or more unique codes in different schemes.

A binary coding scheme combining a first SCNC population having an emission wavelength within a 490–565 nm channel and a second SCNC population within a 575–650 nm channel produces 3000 valid codes using 1-nm resolved SCNC populations if a minimum peak separation of 75 nm is used. The system can be expanded to include many peaks, the only requirement being that the minimum separation between peak wavelengths in valid codes is sufficient to allow their resolution by the detection methods used in that application.

A binary code using a spectral bandwidth of 300 nm, a coding-peak resolution, i.e., the minimum step size for a peak within a single channel, of 4 nm, a minimum interpeak spacing of 50 nm, and a maximum of 6 peaks in each code results in approximately 200,000 different codes. This assumes a purely binary code, in which the peak within each channel is either "on" or "off." By adding a second "on" intensity, i.e., wherein intensity is 0, 1 or 2, the number of potential codes increases to approximately 5 million. If the coding-peak resolution is reduced to 1 nm, the number of codes increases to approximately $1 \times 10^{10}$.

Valid codes within a given coding scheme can be identified using an algorithm. Potential codes are represented as a binary code, with the number of digits in the code corresponding to the total number of different SCNC populations having different peak wavelengths used for the coding scheme. For example, a 16-bit code could represent 16 different SCNC populations having peak emission wavelengths from 500 nm through 575 nm, at 5 nm spacing. A binary code 1000 0000 0000 0001 in this scheme represents the presence of the 500 nm and 575 nm peaks. Each of these 16-bit numbers can be evaluated for validity, depending on the spacing that is required between adjacent peaks; for example, 0010 0100 0000 0000 is a valid code if peaks spaced by 15 nm or greater can be resolved, but is not valid if the minimum spacing between adjacent peaks must be 20 nm. Using a 16-bit code with 500 to 575 nm range and 5 nm spacing between peaks, the different number of possible valid codes for different minimum spectral spacings between adjacent peaks is shown in Table 1.

TABLE 1

The number of unique codes with a binary 16-bit system.

| Spectral Separation | 5 nm | 10 nm | 15 nm | 20 nm | 25 nm | 30 nm |
|---|---|---|---|---|---|---|
| Number of unique codes | 65535 | 2583 | 594 | 249 | 139 | 91 |

If different distinguishable intensities are used, then the number of valid codes dramatically increases. For example, using the 16-bit code above, with 15 nm minimum spacing between adjacent peaks in a code, 7,372 different valid codes are possible if two intensities, i.e., a ternary system, are used for each peak, and 38,154 different valid codes are possible for a quaternary system, i.e., wherein three "on" intensities can be distinguished.

Codes utilizing intensities require either precise matching of excitation sources or incorporation of an internal intensity standard into the beads due to the variation in extinction coefficient exhibited by individual SCNCs when excited by different wavelengths.

It is preferred that the light source used for the encoding procedure be as similar as possible (preferably of the same wavelength and intensity) to the light source that will be used for decoding. The light source may be related in a quantitative manner, so that the emission spectrum of the final material may be deduced from the spectrum of the staining solution.

Labels

Labels useful in the invention described herein include any substance which can be detected in association with the substrate when the molecule to which the label is attached, directly or indirectly, is bound to the capture probe which is attached to the substrate. Any effective detection method can be used, including optical, spectroscopic, electrical, piezoelectrical, magnetic, Raman scattering, surface plasmon resonance, radiographic, calorimetric, calorimetric, etc.

The label comprises an agent selected from a chromophore, a lumiphore, a fluorophore, a chromogen, a hapten, an antigen, a radioactive isotope, a magnetic particle, a metal nanoparticle such as a gold or silver nanoparticle, an enzyme, an antibody or binding portion or equivalent thereof, an aptamer, one member of a binding pair, and combinations thereof.

A fluorophore can be any substance which absorbs light of one wavelength and emits light of a different wavelength. Typical fluorophores include fluorescent dyes, semiconductor nanocrystals, lanthanide chelates, and a green fluorescent protein.

Exemplary semiconductor nanocrystals include those SCNCs described above. Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4', 5'-dichloro-2', 7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluorg 633, Alexa Fluor® 647, Alexa Fluor® 660, Alexa Fluor® 680, 7-amino-4methylcoumarin-3-acetic acid, BODIPY FL, BODIPY FL-Br$_2$, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Exemplary lanthanide chelates include europium chelates, terbium chelates and samarium chelates.

The term "green fluorescent protein" refers to both native Aequorea green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151–154; Heim, R. et al, (1994) *Proc. Natl. Acad. Sci. USA* 91:12501–12504; Heim, R. et al. (1995) Nature 373:663–664). Delgrave et al. isolated mutants of cloned Aequorea victoria GFP that had red-shifted excitation spectra. Bio/Technology 13:151–154 (1995). Heim, R. et al. reported a mutant (Tyr66 to His) having a blue fluorescence (*Proc. Natl. Acad. Sci.* (1994) USA 91:12501–12504).

Exemplary enzymes include alkaline phosphatase, horseradish peroxidase, β-galactosidase, glucose oxidase, galactose oxidase, neuraminidase, a bacterial luciferase, an insect luciferase and sea pansy luciferase (Renilia koeflikeri), which can create a detectable signal in the presence of suitable substrates and assay conditions, known in the art.

Exemplary haptens and/or members of a binding pair include avidin, streptavidin, digoxigenin, biotin, and those described above.

Production of SCNCs

SCNCs can be made from any material and by any technique that produces SCNCs having emission characteristics useful in the methods, articles and compositions taught herein. The SCNCs have absorption and emission spectra that depend on their size, size distribution and composition. Suitable methods of production are disclosed in U.S. Pats. Nos. 6,048,616; 5,990,479; 5,690,807; 5,505,928; 5,262,357; PCT Publication No. WO 99/26299 (published May 27, 1999; inventors Bawendi et al.); Murray et al. (1993) J. Am. Chem. Soc. 115:8706–8715; and Guzelian et al. (1996) J. Phys. Chem. 100:7212–7219.

Examples of materials from which SCNCs can be formed include group II–VI III–V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, hAs, InSb, AIS, AIP, AlSb, Pb, Ge, Si, and other materials such as PbS, PbSe, and mixtures of two or more semiconducting materials, and alloys of any semiconducting material(s).

The composition, size and size distribution of the semiconductor nanocrystal affect its absorption and emission spectra. Exemplary SCNCs that emit energy in the visible range include CdS, CdSe, CdTe, ZnSe, ZnTe, GaP, and GaAs. Exemplary SCNCs that emit energy in the near IR range include InP, InAs, InSb, PbS, and PbSe. Exemplary SCNCs that emit energy in the blue to near-ultraviolet include ZnS and GaN. The size of SCNCs in a given population can be determined by the synthetic scheme used and/or through use of separation schemes, including for example size-selective precipitation and/or centrifugation. The separation schemes can be employed at an intermediate step in the synthetic scheme or after synthesis has been completed. For a given composition, larger SCNCs absorb and emit light at longer wavelengths than smaller SCNCs. SCNCs absorb strongly in the visible and UV and can be excited efficiently at wavelengths shorter than their emission peak. This characteristic allows the use in a mixed population of SCNCs of a single excitation source to excite all the SCNCs if the source has a shorter wavelength than the shortest SCNC emission wavelength within the mixture; it also confers the ability to selectively excite subpopulation(s) of SCNCs within the mixture by judicious choice of excitation wavelength.

The surface of the SCNC is preferably modified to enhance emission efficiency by adding an overcoating layer to form a "shell" around the "core" SCNC, because defects in the surface of the core SCNC can trap electrons or holes and degrade its electrical and optical properties. Addition of an insulating shell layer removes nonradiative relaxation pathways from the excited core, resulting in higher luminescence efficiency. Suitable materials for the shell include semiconductor materials having a higher bandgap energy than the core and preferably also having good conductance and valence band offset. Thus, the conductance band of the shell is desirably of a higher energy and the valence band is desirably of a lower energy than those of the core. For SCNC cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet may be used for the shell, for example ZnS, GaN, and magnesium chalcogenides, e.g., MgS, MgSe, and MgTe. For an SCNC core that emits in the near IR, materials having a bandgap energy in the visible, such as CdS or CdSe, or the ultraviolet may be used. Preparation of core-shell SCNCs is described in, e.g., Dabbousi et al. (1997) J. Phys. Chem. B 101:9463; Kuno et al., J. Phys. Chem. 106:9869 (1997); Hines et al., J. Phys. Chem. 100:468; PCT Publ. No. WO 99/26299; and U.S. Pat. No. 6,207,229 to Bawendi et al. issued Mar. 27, 2001. The SCNCs can be made further luminescent through overcoating procedures as described in Danek et al. (1996) Chem. Mat. 8(1):173-180, and Peng et al. (1997) J. Am. Chem. Soc. 119:7019-7029.

Most SCNCs are typically prepared in coordinating solvent, such as TOPO and trioctyl phosphine (TOP), resulting in the formation of a passivating organic layer on the surface of SCNCs with and without a shell. Such passivated SCNCs can be readily solubilized in organic solvents, for example toluene, chloroform and hexane. Molecules in the passivating layer can be displaced or modified to provide an outermost coating that adapts the SCNCs for use in other solvent systems, for example aqueous systems.

Alternatively, an outermost layer of an inorganic material such as silica can be added around the shell to improve the aqueous dispersibility of the SCNCs, and the surface of the silica can optionally be derivatized (Bruchez et al., Science 281:2013 (1998)).

A displacement reaction may also be employed to modify the SCNC to improve the solubility in a particular organic solvent. For example, if it is desired to associate the SCNCs with a particular solvent or liquid, such as pyridine, the surface can be specifically modified with pyridine or pyridine-like moieties which are soluble or miscible with pyridine to ensure solvation. Water-dispersible SCNCs can be prepared as described in Bawendi et al., PCT Publ. No. WO 00/17655, published Mar. 30, 2000.

The surface layer of the SCNCs may be modified by displacement to render the SCNC reactive for a particular coupling reaction. For example, displacement of trioctylphosphine oxide (TOPO) moieties with a group containing a carboxylic acid moiety enables the reaction of the modified SCNCs with amine containing moieties to provide an amide linkage. For a detailed description of these linking reactions, see, e.g., U.S. Pat. No. 5,990,479; Bruchez et al. (1998) Science 281:2013–2016, Chan et al. (1998) Science 281:2016–2018, Bruchez "Luminescent SCNCs: Intermittent Behavior and use as Fluorescent Biological Probes" (1998) Doctoral dissertation, University of California, Berkeley, and Mikulec "SCNC Colloids: Manganese Doped Cadmium Selenide, (Core)Shell Composites for Biological Labeling, and Highly Fluorescent Cadmium Telluride" (1999) Doctoral dissertation, Massachusetts Institute of Technology. The SCNC may be conjugated to other moieties directly or indirectly through a linker.

Examples of suitable spacers or linkers are polyethyleneglycols, dicarboxylic acids, polyamines and alkylenes. The spacers or linkers are optionally substituted with functional groups, for example hydrophilic groups such as amines, carboxylic acids and alcohols or lower alkoxy group such as methoxy and ethoxy groups. Additionally, the spacers will have an active site on or near a distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., Solid Phase Peptide Synthesis, IRL Press (1989).

The Excitation Source

By exposing the encoded beads or other substrate prepared and described as above to light of an excitation source, the SCNCs disposed in the material will be excited to emit light. This excitation source is of an energy capable of exciting at least one population of SCNCs used in the experiment to emit light and preferably chosen to be of higher energy than the shortest emission wavelength of the SCNCs used. Further, the excitation source can be chosen such that it excites a minimum number of SCNCs in the sample to produce detectable light. Preferably the excitation source will excite a sufficient number of different populations of SCNCs to allow unique identification of all the encoded materials used in the experiment. For example, using two different populations of beads having different ratios of red to blue SCNCs, it would not be sufficient to only excite the red emitting SCNCs, e.g., by using green or yellow light, of the sample in order to decode the beads. It would be necessary to use a light source comprising at least one wavelength that is capable of exciting the blue emitting and the red emitting SCNCs simultaneously, e.g., violet or ultraviolet. There may be one or more light sources used to excite the different populations of SCNCs simultaneously, or sequentially, but a given light source will only excite subpopulations of SCNCs that emit at lower energy than the light source, due to the absorbance spectra of the SCNCs.

In addition, if a lamp source is used, degradation of the lamp can result in changes in the excitation source, thereby compromising the codes.

Detection of SCNC Emission

An example of an imaging system for automated detection for use with the present methods comprises an excitation source, a monochromator (or any device capable of spectrally resolving the image, or a set of narrow band filters) and a detector array. The excitation source can comprise blue or UV wavelengths shorter than the emission wavelength(s) to be detected. This may be: a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm) or a HeCd laser; solid state diode lasers in the blue such as GaN and GaAs (doubled) based lasers or the doubled or tripled output of YAG or YLF based lasers; or any of the pulsed lasers with output in the blue.

The emitted light can be detected with a device that provides spectral information for the substrate, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, or electronically tunable filters are appropriate). More than one imager may be used to gather data simultaneously through dedicated filters, or the filter may be changed in front of a single imager. Imaging based systems, like the Biometric Imaging system, scan a surface to find fluorescent signals.

A scanning system can be used in which the sample to be analyzed is scanned with respect to a microscope objective. The luminescence is put through a single monochromator or a grating or prism to spectrally resolve the colors. The detector is a diode array that then records the colors that are emitted at a particular spatial position. The software then recreates the scanned image.

Decoding Multiple Fluorescence Emissions

When imaging samples labeled with multiple fluorophores, it is desirable to resolve spectrally the fluorescence from each discrete region within the sample. Such samples can arise, for example, from multiple types of SCNCs (and/or other fluorophores) being used to encode beads, from a single type of SCNC being used to encode beads but bound to a molecule labeled with a different fluorophore, or from multiple molecules labeled with different types of fluorophores bound at a single location. Decoding the spectral code of an encoded substrate can take place prior to, simultaneously with, or subsequent to determining whether a label from an amplification product is associated with the substrate.

Many techniques have been developed to solve this problem, including Fourier transform spectral imaging (Malik et al. (1996) J. Microsc. 182:133; Brenan et al. (1994) Appl. Opt. 33:7520) and Hadamard transform spectral imaging (Treado et al. (1989) Anal. Chem. 61:732A; Treado et al. (1990) Appl. Spectrosc. 44:1–4; Treado et al. (1990) Appl. Spectrosc. 44:1270; Hammaker et al. (1995) J. Mol. Struct. 348;135; Mei et al. (1996) J. Anal. Chem. 354:250; Flateley et al. (1993) Appl. Spectrosc. 47:1464), imaging through variable interference (Youvan (1994) Nature 369:79; Goldman et al. (1992) Biotechnology 10:1557), acousto-optical (Mortensen et al. (1996) IEEE Trans. Inst. Meas. 45:394; Turner et al. (1996) Appl. Spectrosc. 50:277) or liquid crystal filters (Morris et al. (1994) Appl. Spectrosc. 48:857) or simply scanning a slit or point across the sample surface (Colarusso et al. (1998) Appl. Spectrosc. 52:106A), all of which are capable of generating spectral and spatial information across a two-dimensional region of a sample.

One-dimensional spectral imaging can easily be achieved by projecting a fluorescent image onto the entrance slit of a linear spectrometer. In this configuration, spatial information is retained along the y-axis, while spectral information is dispersed along the x-axis (Empedocles et al. (1996) Phys. Rev. Lett. 77(18):3873). The entrance slit restricts the spatial position of the light entering the spectrometer, defining the calibration for each spectrum. The width of the entrance slit, in part, defines the spectral resolution of the system.

Two-dimensional images can be obtained by eliminating the entrance slit and allowing the discrete images from individual points to define the spatial position of the light entering the spectrometer. In this case, the spectral resolution of the system is defined, in part, by the size of the discrete images. Since the spatial position of the light from each point varies across the x-axis, however, the calibration for each spectrum will be different, resulting in an error in the absolute energy values. Splitting the original image and passing one half through a dispersive grating to create a separate image and spectra can eliminate this calibration error. With appropriate alignment, a correlation can be made between the spatial position and the absolute spectral energy.

To avoid ambiguity between images that fall along the same horizontal line, a second beam-splitter can be added, with a second dispersive element oriented at 90 degrees to the original. By dispersing the image along two orthogonal directions, it is possible to unambiguously distinguish the spectra from each discrete point within the image. The spectral dispersion can be performed using gratings, for example holographic transmission gratings or standard reflection gratings. For example, using holographic transmission gratings, the original image is split into 2 (or 3) images at ratios that provide more light to the spectrally dispersed images, which have several sources of light loss, than the direct image. This method can be used to spectrally image a sample containing discrete point signals, for example in high throughput screening of discrete spectral images such as single molecules or ensembles of molecules immobilized on a substrate, and for highly parallel reading of spectrally encoded beads. The images are then projected onto a detector and the signals are recombined to produce an image that contains information about the amount of light within each band-pass.

Alternatively, techniques for calibrating point spectra within a two-dimensional image are unnecessary if an internal wavelength reference (the "reference channel") is included within the spectrally encoded material. The reference channel is preferably either the longest or shortest wavelength emitting fluorophore in the code. The known emission wavelength of the reference channel allows determination of the emission wavelengths of the fluorophores in the dispersed spectral code image. In addition to wavelength calibration, the reference channel can serve as an intensity calibration where coding schemes with multiple intensities at single emission wavelengths are used. Additionally, a fixed intensity of the reference channel can also be used as an internal calibration standard for the quantity of label bound to the surface of each bead.

In one system for reading spectrally encoded beads or materials, a confocal excitation source is scanned across the surface of a sample. When the source passes over an encoded bead, the fluorescence spectrum is acquired. By raster-scanning the point-excitation source over the sample, all of the beads within a sample can be read sequentially.

Optical tweezers can optionally be used to "sweep" spectrally encoded beads or any other type of bead into an ordered array as the beads are read. The "tweezers" can either be an infrared laser that does not excite any fluorophores within the beads, or a red laser that simultaneously traps the beads and also excites the fluorophores.

Optical tweezers can be focused to a tight spot in order to hold a micron-size bead at the center of this spot by "light pressure." Any bead smaller than approximately 10 $\mu$m in diameter that comes in contact with the focused spot will be pulled into the point of highest intensity. For beads that are larger than about 0.5 $\mu$m, only one bead can exist within the "trap" at a time. See, e.g., Ashkin (1997) *Proc. Natl. Acad. Sci USA* 94:4853–4860; Helmerson et al. (1997) *Clin. Chem.* 43:379–383; Quake et al. (1977) *Nature* (London) 388:151–154; Ashkin (1972) *Sci. Amer.* 226:63–71; Ashkin (1970) *Phys. Rev. Lett.* 24:156–159.

Optical tweezers can be used to hold spectrally encoded beads and to order them for reading. The tweezers can be focused near the bottom of a well located at the center of the detection region of a point-scanning reader, which can use the same optical path. The reader and tweezers can be scanned together so that they are always in the same position relative to each other.

For example, if the tweezers are turned on at spot-1, any bead contacted by the tweezers will be pulled into the center of the trap, ensuring an accurate quantitative measure of the assay label intensity. After reading the first bead, the tweezers are turned off to release it, and the scanner advances to the right just far enough to prevent the first bead from being retrapped before the tweezers are turned on again and then moved immediately to spot-2. In the process, any bead contacted by the tweezers would be trapped and brought to spot-2, where it is read. Choosing a scan distance that corresponds to the average interbead spacing can minimize bead loss from multiple beads occurring between sampling points.

Alternatively, the optical tweezers can be focused within the solution away from the surface of the well. As the tweezers are turned on and off, the solution is mixed, so that different beads are brought into the detection region and held while they are scanned.

In another alternative, the optical tweezers can be focused in only one dimension, i.e., to a line rather than a spot, thus creating a linear trap region. This type of system can be used to sweep beads into distinct lines that can be scanned by a "line scanning" bead reader.

SNP Detection Using Encoded Beads

Figure 2:
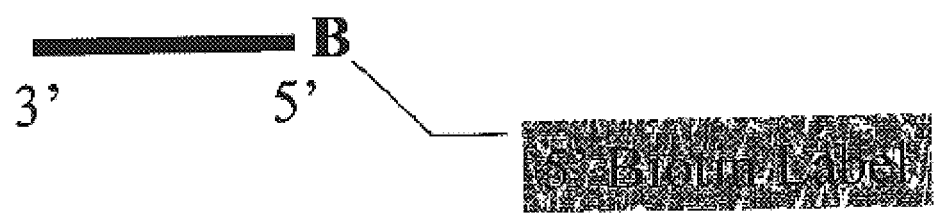
FIG. 2 depicts a labeled second primer which can be used with the first primer shown in FIG. 1 to amplify a target polynucleotide in a polymerase chain reaction.
Figure 3:
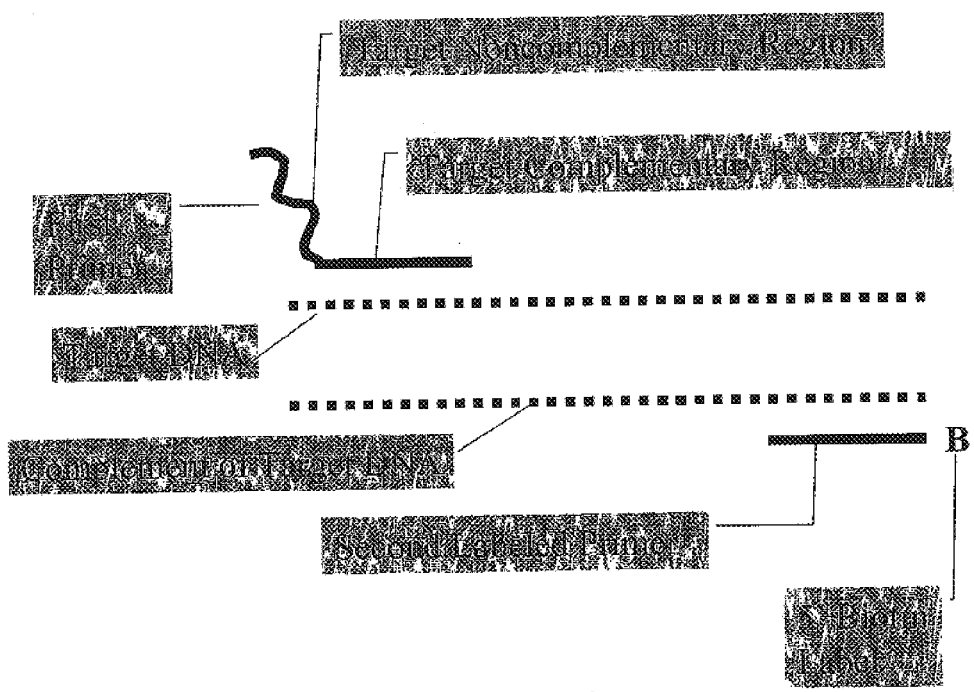
FIG. 3 depicts the first and second primers shown in FIGS. 1 and 2 hybridized to opposite strands of double-stranded DNA. The target polynucleotide is the strand to which the first primer hybridizes, while the second primer hybridizes to the complementary strand to the target.
Figure 4:
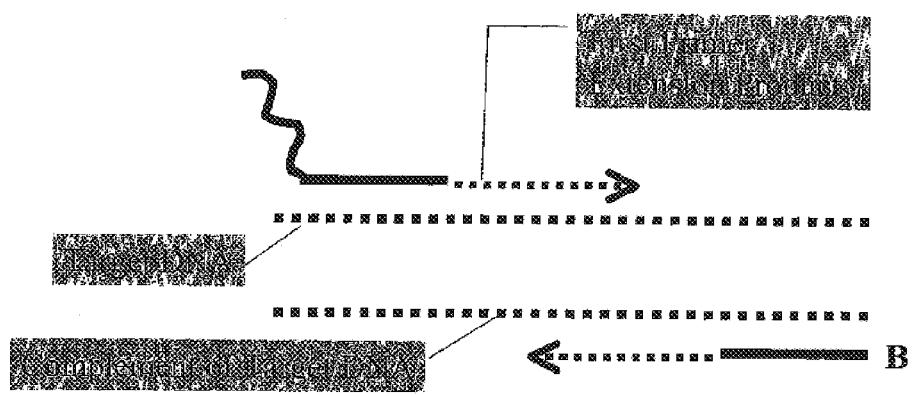
FIG. 4 depicts the extension of the first and second primers from the complementary strands of the double-stranded DNA. Extension of the first primer forms a first primer extension product. Extension of the second primer from the complement of the target polynucleotide does not result in a detectable amplification product, as the extension product thus formed does not comprise a capture sequence that is complementary to the target noncomplementary region in the first primer.

A first oligonucleotide primer is synthesized that comprises at its 3' end a target complementary region that is complementary to a predetermined target polynucleotide, and also comprises a target noncomplementary region that is not complementary to the target polynucleotide, typically at its 5' end (see FIG. 1). A second reverse oligonucleotide primer is synthesized comprising a label as described above including an SCNC, here shown as a 5' biotin label (see FIG. 2). These two primers are used in a polymerase chain reaction (PCR) to amplify a target sequence of DNA (see FIGS. 3 and 4). The first primer hybridizes to the target DNA and is extended by a polymerase to form a first primer extension product (PEP) that comprises the target noncomplementary region.

Figure 5:
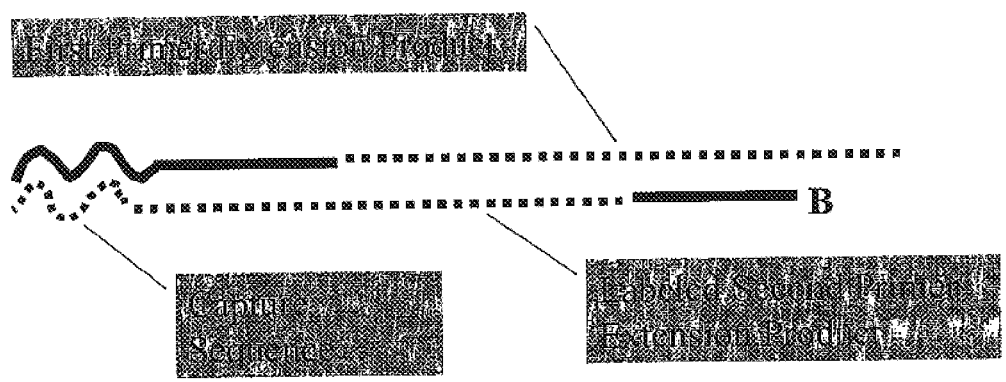
FIG. 5 depicts the formation of a labeled second primer extension product resulting from extension of the labeled second primer shown in FIG. 2 upon hybridization to the first primer extension product. The second primer extension product thus produced comprises a capture sequence that is complementary to the target noncomplementary sequence in the first primer, as depicted by the dashed curve at its 3' end.

In the second, and subsequent, rounds of PCR, the second labeled reverse primer can hybridize to the first primer extension product and be extended to form a second primer extension product (see FIG. 5). This second PEP comprises the second labeled primer at its 5' end and a capture sequence which is the complement of the target noncomplementary region in the first primer. In this scheme, the label and the capture sequence only become linked when target DNA is present in the sample to be amplified (see FIG. 5). (The second labeled primer can also hybridize to the complementary strand to the target DNA and be extended, but this extension product is not detected in this scheme, as it does not comprise a capture sequence.)

Figure 6:
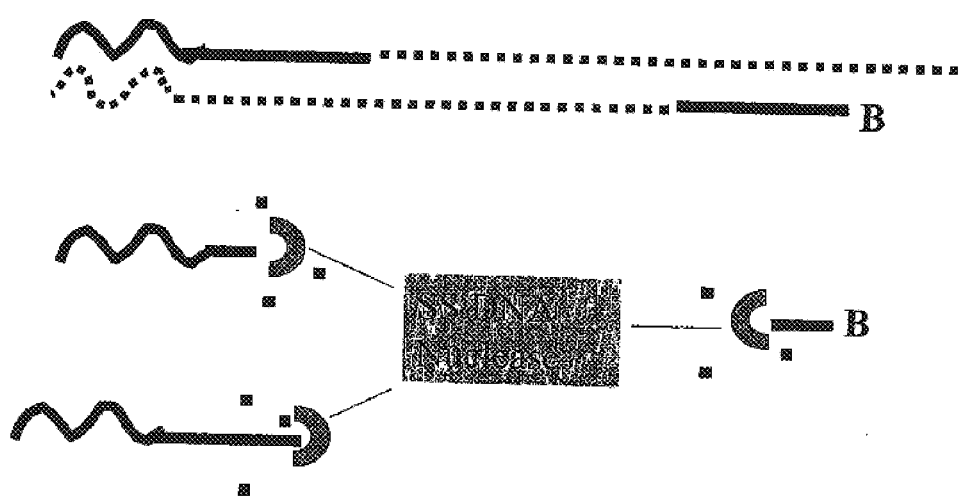
FIG. 6 depicts the digestion of unincorporated primers with a single-stranded DNA nuclease after amplification and prior to capture of the labeled second primer extension product.
Figure 7:
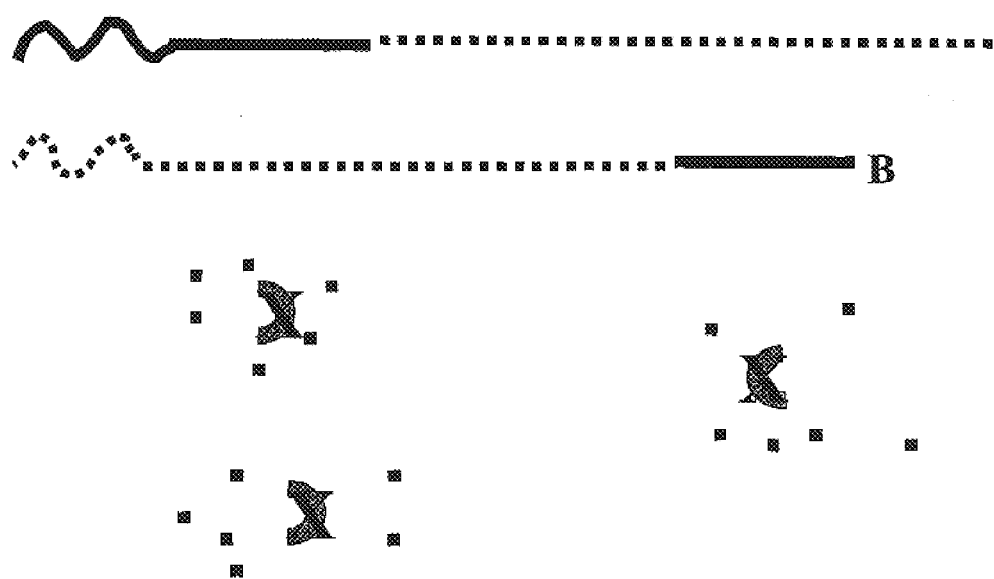
FIG. 7 depicts the inactivation by heating of the single-stranded DNA nuclease after digestion of single-stranded DNA in the mixture, including unincorporated first and second primers, but prior to dissociation of the first and second primer extension products.

After the PCR amplification is completed, the solution can optionally be treated to eliminate any single-stranded DNA, for example with a single-stranded DNA nuclease (see FIG. 6). This removes single-stranded polynucleotides such as the unincorporated primers; unincorporated first primer could later compete with capture of the second primer extension product by the encoded bead conjugate. Preferably the nuclease used is thermolabile. The amplification solution is then heat-treated (e.g. 95° C. for ten minutes). This heat treatment serves two purposes: first, the elevated temperature reduces the nuclease activity by denaturing the thermolabile protein; and, second, it dissociates the complementary first and second PEPs to single-strands so that the second PEP is then available for subsequent hybridization (see FIG. 7).

Figure 8:
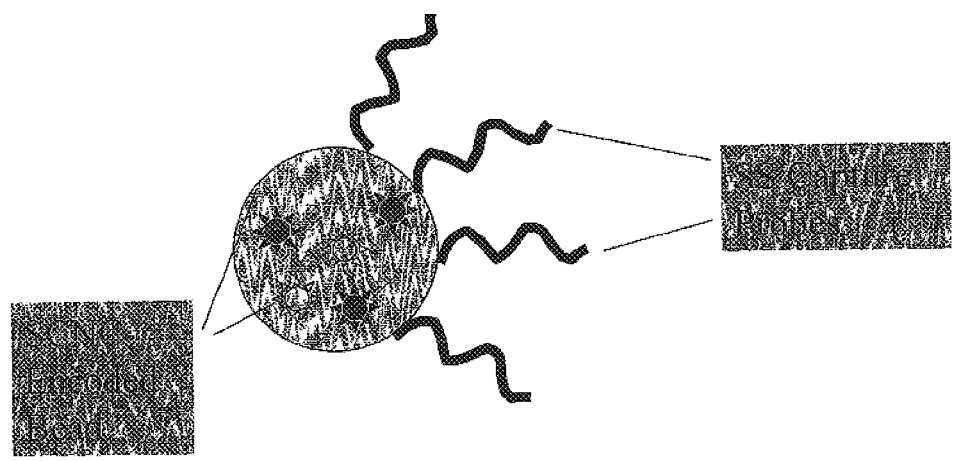
FIG. 8 depicts a microsphere encoded with a semiconductor nanocrystal code and conjugated to single-stranded capture probes that are complementary to the capture sequence. This conjugate is referred to as an encoded bead conjugate.

A batch of spectrally encoded beads with known fluorescence characteristics is created by imbedding semiconductor nanocrystals into microspheres as described above (see FIG. 8). The beads can be prepared having a functional chemical group (e.g. a carboxyl group) on the surface. A generic polynucleotide capture probe can be chemically synthesized to have a predetermined nucleotide sequence that can hybridize to the capture sequence in the second primer extension product and a functionalized linker (e.g., a 3' or 5' amino linker) that allows it to be attached covalently to the spectrally encoded beads, and then purified. The oligonucleotide capture probe is chemically conjugated to the surface of the spectrally encoded beads to form an encoded bead conjugate using any suitable method (e.g., covalent attachment of an amino-labeled oligonucleotide onto carboxylated beads in the presence of EDC). See FIG. 8.

Figure 9:
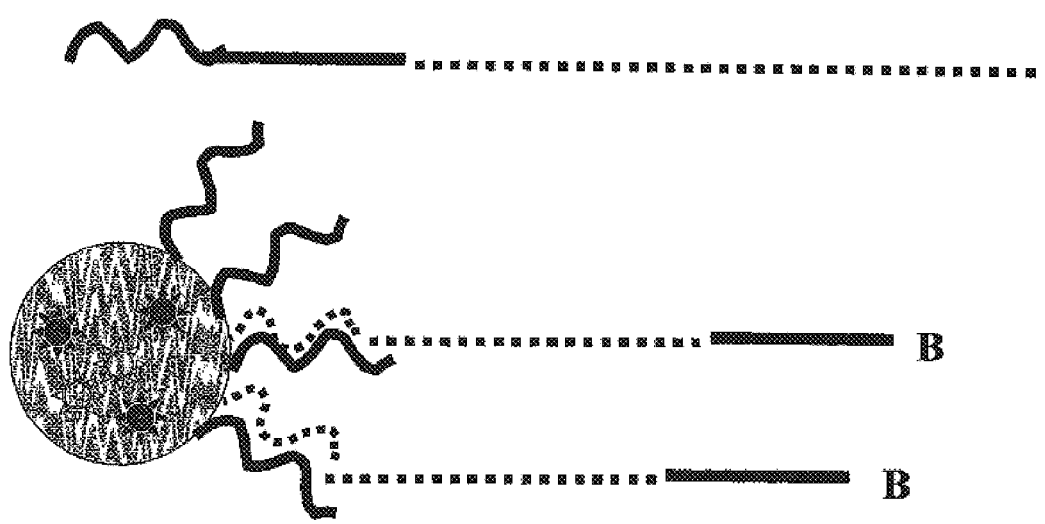
FIG. 9 depicts the capture of the second primer extension product by the encoded bead conjugate via hybridization of the capture sequence to the capture probe.
Figure 10:
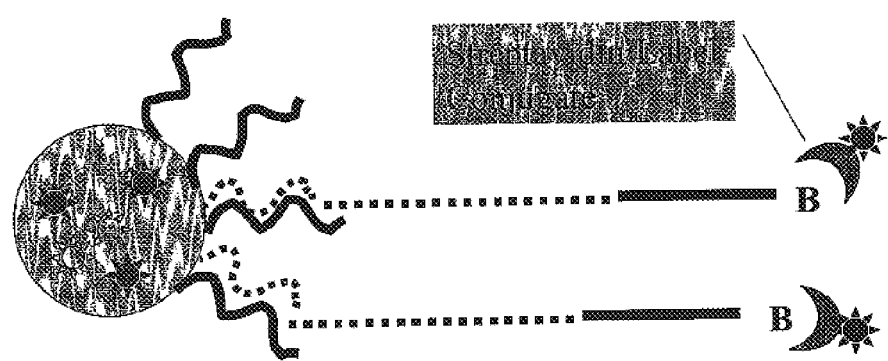
FIG. 10 depicts the binding of a streptavidin/semiconductor nanocrystal conjugate to the biotin label on the second primer extension product bound to the encoded bead conjugate.

The encoded bead conjugates are then incubated with the amplification reaction mixture. If the target polynucleotide was present in the sample and the second primer extension product comprising the capture sequence was produced during the amplification reaction, the second PEP will hybridize to the capture probe on the surface of the encoded bead conjugate (or other substrate) during this incubation to form an amplification product detection complex (see FIG. 9). If the label on the second PEP is to be indirectly detected, for example where the second primer is biotin-labeled, the second PEP must be linked to a detectable label, for example by contacting a conjugate of a biotin-binding molecule such as streptavidin and a directly detectable label such as a detectable semiconductor nanocrystal or phycoerythrin (see FIG. 10). Association of the detectable label with the encoded bead conjugate can then be detected and optionally quantitated.

This assay can be multiplexed, i.e., multiple distinct assays can be run simultaneously, by using different pairs of primers to detect multiple single nucleotide polymorphisms (SNPs) within a sample. Allele-specific priming can be used to distinguish between alleles of individual SNPs in the same reaction. Either the first or second primer can be the selective allele-specific primer comprising a 3' end designed to overlap the location of the SNP by 1–5 nucleotides. If the selective primer is completely complementary to the target sequence, it will anneal and extend. If the selective primer has a mismatch at the location of the SNP, it may partially anneal but cannot be extended, or is extended at a much lower efficiency.

Where the second primer is the selective primer, it must be labeled with a different label than the second primer for the other allele, because both alleles will use the same first primer comprising the same unique sequence and thus the second primer extension products from the two alleles will not be distinguishable by their different capture sequences.

Figure 11:
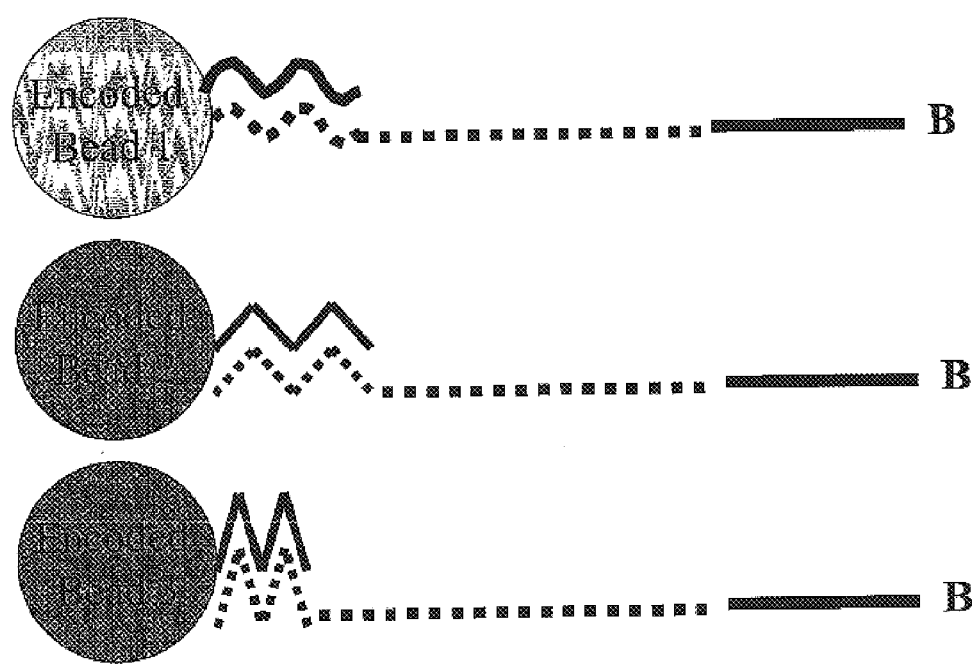
FIG. 11 depicts a multiplex assay using three different encoded bead conjugates, each different conjugate comprising a different capture probe, to simultaneously assay for three different amplification products, each different amplification product comprising a different capture sequence which can hybridize to its corresponding capture probe.
Figure 12:
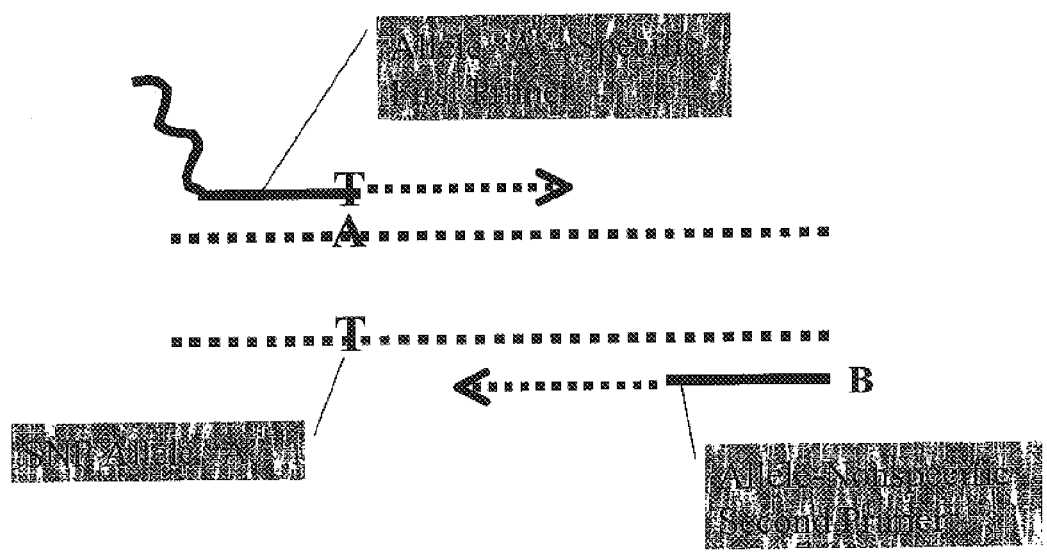
FIG. 12 depicts an allele-specific amplification reaction for assaying a target polynucleotide from one allele of a single nucleotide polymorphism by a method of the invention.
Figure 13:
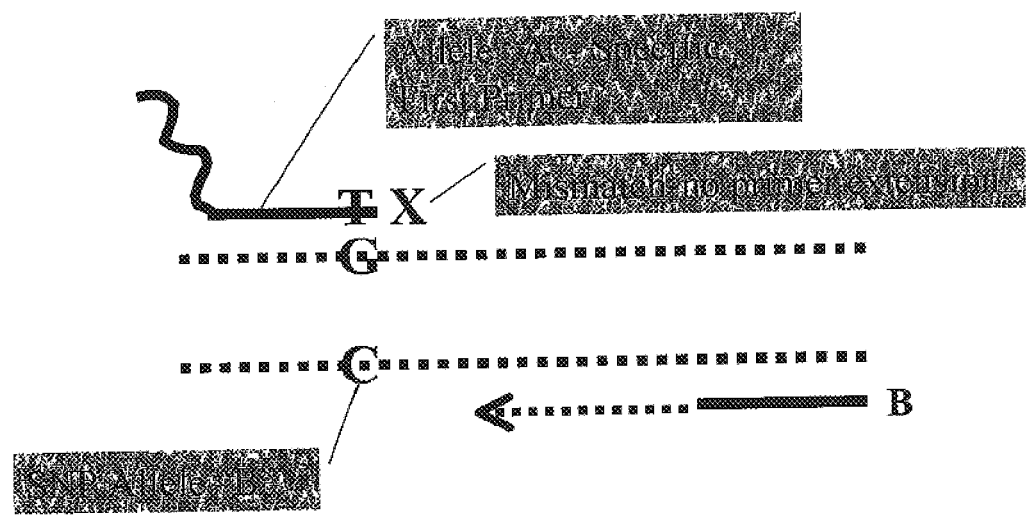
FIG. 13 depicts the lack of extension of an allele-specific first primer upon hybridization to a noncomplementary allele. With no formation of first primer extension product from the mismatched target polynucleotide, no second primer extension product comprising the capture sequence will be formed and no signal will be obtained from the corresponding encoded bead conjugate. This can inhibit efficient amplification from a sample containing both matched and mismatched alleles to the primer pairs being used.
Figure 14:
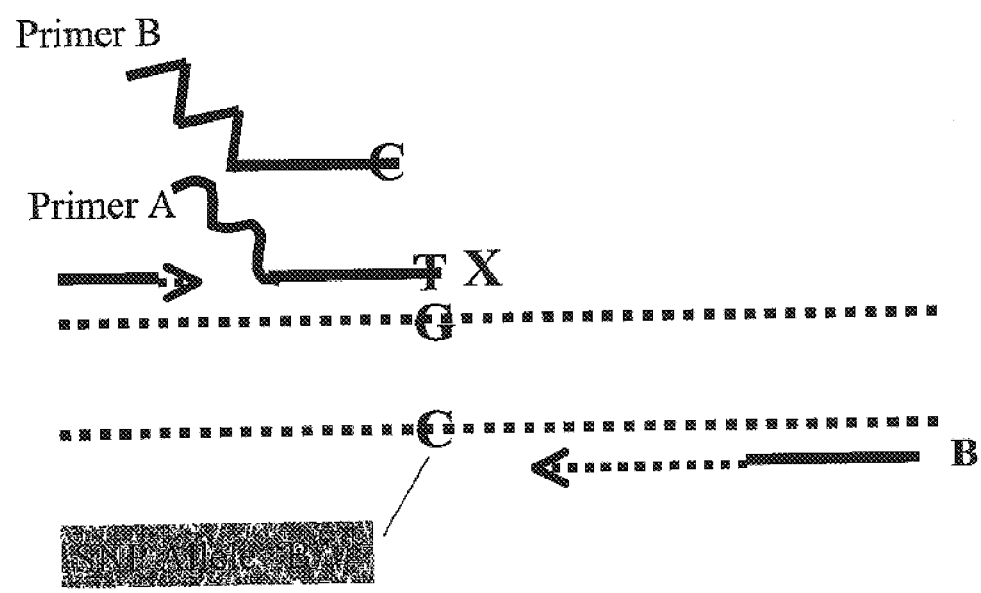
FIG. 14 depicts the use of a primer upstream from the allele-specific primer to amplify a segment of the target polynucleotide and thereby increase its copy number and thus permit a higher level of allele-specific amplification to take place when both matched and mismatched allele-specific alleles are present.

Alternatively, where the first primer is selective, each allele-specific first primer comprises a unique target noncomplementary region. Batches of beads containing different spectral codes are separately conjugated to different capture probes specific for corresponding different capture sequences (see FIG. 11). When a first primer is extended, its unique target noncomplementary region becomes incorporated into that first primer extension product (see FIG. 12). The second primer is 5' end-labeled (e.g., with biotin or fluorescein) during synthesis, and is used in conjunction with the selective first primer to perform an allele-specific PCR (see FIG. 12). A target polynucleotide containing the noncomplementary allele will not be significantly amplified, due to the mismatch under the primer sequence (see FIG. 13). By using a different unique target noncomplementary region in each sequence-specific first primer, it can be ensured that a unique capture sequence will be incorporated into the second PEP (see FIGS. 12–14).

The incorporation of unique capture sequences into the second PEPs from the two alleles when using selective first primers provides an additional benefit. The sequences of the two SNPs initially differ by a single nucleotide. The second primer extension products made from the two alleles differ by both the single nucleotide polymorphism and by the different capture sequences. Therefore, assuming that the initial priming events are predominantly allele-specific, the resultant second primer extension products will contain sequence differences that are much more pronounced. This can be exploited to increase the specificity of the allele-specific amplification. For example, the target complementary region of the allele-specific first primer can be shortened by several nucleotides, enhancing the difference in melting temperature between the alleles. The annealing temperature can then be increased during PCR after formation of the second PEP, resulting in improved specificity with no loss of amplification efficiency. This attribute by itself constitutes a fundamental improvement in polymorphism-specific PCR, and can be used in assaying for other types of sequence variations beyond SNPs.

Use of the Methods with Microarrays

Microarray slides attached to capture probe polynucleotides can be prepared as described at www.nhgri.nih.gov/DIR/Microarray/fabrication.html, also set forth in U.S. Pat. App. Ser. No. 09/675,528 by Empedocles et al. entitled "Microarray Methods Utilizing Semiconductor Nanocrystals", filed Sep. 29, 2000. Further guidance on fabrication, sample labeling and conditions for hybridization using microarrays is provided, for example, by Bittner M., et al. (2000) Nature 406:536–540; Khan J., et al. (1999) Electrophoresis 20:223–9; Duggan, D. J. (1999) Science 283:83–87; and DeRisi, J. et al. (1996) Nature Genet 14:457–60.

In a typical microarray experiment, the sample suspected of containing the target polynucleotide is treated to form a labeled amplification product. The amplification products are optionally mixed with blockers, for example tRNA, Cot1 DNA, or purified repeat sequences such as LINE or Alu sequences, or mixtures thereof. Nonnucleotide blocking agents can also be used, including proteins, for example BSA, and detergents. This mixture is then incubated with the microarray slides. The slides are then rinsed.

The microarray can then be scanned with a laser scanner having an excitation source and emission filters appropriate for the particular SCNC(s) or other fluorophore used, or the microarray can be scanned with a wide-field imaging scanner having appropriate excitation and emission filters.

Kits

Kits comprising reagents useful for performing the methods of the invention are also provided. In one embodiment, a kit comprises a substrate attached to a capture probe and first and second primers for amplifying the target polynucleotide. The substrate can be an encoded bead comprising a first spectral code comprising a first semiconductor nanocrystal and first fluorescence characteristics. The capture probe can bind to the amplification product produced from the target polynucleotide, and a sample may be assayed for the presence of such a target polynucleotide or amplification product produced therefrom using the components of the kit.

The second primer can be labeled, or the kit may comprise a reagent for incorporating a label into the amplification product, such as a labeled nucleotide. The components of the kit are retained by a housing. Instructions for using the kit to perform a method of the invention are provided with the housing, and may be located inside the housing or outside the housing, and may be printed on the interior or exterior of any surface forming the housing which renders the instructions legible. The kit may be in multiplex form, containing pluralities of one or more different substrates or pairs of primers. The substrate may comprise a plurality of polynucleotides of different sequence for performing a plurality of individual assays thereon such as a microarray, or a plurality of different beads can be provided for a multiplexed assay wherein each of the different beads comprises a different capture probe for binding to a corresponding different amplification product.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Spectrally Encoding and Functionalizing Microspheres

The following experiment was performed to prepare encoded and functionalized microspheres via a heat-swelling method and Dextran Biotin coating.

Materials:
  a. 10 um Bangs COOH functionalized beads 10% solid (Bangs Lab)
  b. 10 mM PBS, pH 7.4 (Sigma)
  c. 10 mM PBS/1% BSA
  d. Dihydrolipoic acid (DHLA)-derivatized SCNCs (Bawendi et al., PCT Publ. No. WO 00/17655)
  e. Dextran Biotin 10 mg/mL (Sigma); Cat# B5512, Lot# 81H0080
  f. Streptavidin 10 mg/mL (Pierce); Cat# 21 125B, Lot# AH41661

Protocol:
  i. Wash beads three times with PBS buffer and resuspend in PBS to make 5% beads solution
  ii. Heat bead solution in heat block up to ~60° C. with constant mixing
  iii. Add DHLA SCNCs (amount added depends on the intended intensity for the particular beads, determined empirically)
  iv. Incubate the mixture of beads and SCNC for 5–10 min. at 60° C.
  v. Wash encoded beads 3 times with PBS, resuspend in PBS. Check the intensity and uniformity of encoded beads with Facscan and Microscope
  vi. Add Dextran Biotin (10 mg/mL) to encoded beads solution and incubate at room temperature overnight with constant mixing
  vii. Wash biotin dextran-coated encoded beads with PBS and resuspend in PBS/BSA
  viii. Add Streptavidin (final conc. of 5mg/ml) to biotinDextran-coated encoded beads and incubate at room temperature for 3–4 hours.
  ix. Wash SA-encoded beads with PBS and resuspend in PBS/BSA.

SA-encoded beads are ready for attachment of biotinylated Molecular Beacon of choice.

2. Encoding beads with DHLA SCNCs with BSA absorption and functionalizing beads with Streptavidin by Maleimide conjugation

*BSA absorbed on beads provides surface for subsequent absorption of DHLA SCNCs and functional group for conjugation of Streptavidin.

Materials:
  a. 10 um Bangs COOH beads 10% solid (Bangs Lab)
  b. 10 mM PBS/1% BSA, pH 7.4
  c. DHLA SCNCs (of different colors)
  d. Sulfo-SMCC; Cat# 22322, Lot# AF40301, or Sulfo-SMPB (Pierce)
  e. Conjugation buffer & Elution buffer for NAP5 column: 0.1M Sodium Phosphate, 0.15M NaCl, 10 mM EDTA, pH 7.2
  f. NAP5 column equilibration buffer: 10 mM Sodium Phosphate, pH 6.8
  g. NAP5 (Sephadex G25 resin, P harmacia); Cat# 17-0853-02, Lot# 278694
  h. Streptavidin (Pierce); Cat# 21125B, Lot# AH41661
  i. 2-Iminothiolane (Sigma); Cat# I -6256, Lot# 128H1085

Protocol:
  1. Wash beads 3 times with PBS
  2. Add 1% BSA/PBS solution and incubate at room temperature overnight with constant mixing
  3. Wash BSA-coated beads 3 times with PBS
  4. Add DHLA SCNCs and incubate for 15-30 min @RT with constant mixing
  5. Wash off excess DHLA SCNCs with PBS and resuspend [BSA encoded beads] in Conjugation buffer
  *Note: [BSA encoded beads] can be coated with another layer of BSA by incubating these beads with 1% BSA for several hours.
  6. i. Add 2-iminothiolane (20 mg(mL) to [BSA encoded beads]solution. React @ RT for 1–2 hrs with constant mixing. Wash 3 times and resuspend with conjugation buffer
  ii. Maleimide activation of Streptavidin: to 20 mg/mL solution of Streptavidin (in conjugation buffer) added Sulfo-SMCC or Sulfo-SMPB (6 mg/mL). *Note: dissolve Sulfo-SMCC in small amount of dH20 before adding to Streptavidin solution. React @RT for 30 min. (Timing this reaction with iminothiolane reaction above to get purified products at the same time.) Purify Maleimide-activated Streptavidin using NAP5 column with 10–15 mL equilibration buffer (pre-loading) and with 1-2mL elution buffer (post-loading)

Mix purified products from two reactions above and react at Rt for 2-3 hrs. Wash SA-encoded beads with PBS and resuspend in PBS/BSA.

Example 2

Hybridization of Allele-specific PCR Amplicons to Generic Capture Probe Oligonucleotide-Conjugated Beads The following experiment provides allele-specific amplification of genomic DNA from two alleles (A and B) of the LDL receptor using unique target tagged primers. Subsequently the incorporated unique 5' capture sequence was used in sequence specific hybridization to capture probe sequences conjugated to unlabeled beads.

Materials
1. First(forward) Primers(MWG Biotech AG)
   a. LDLrA-GC1s (SEQ ID NO:1)
   b. 5'-GCAATAGGTTTTGAGGGGCATggttgtggaagaggac-3'
   c. LDLrB-GC1a (SEQ ID NO:2)
   5'-TTCTGGGCCACTGACTGATTTggttgtggaagagaac-3'

In the above primers, the unique sequences (target non-complementary regions) are in capital letters and the target-specific complementary region of the primer are in lower-case letters. The polymorphic base is in bold.

2. Second(reverse)Primer(MWG Biotech AG)
   LDLrab
   5'-biotin-TTCAGTGCCAACCGCCTCAC-3'                                           (SEQ ID NO:3)

3. Capture Probes (Biosource International)
   a.    GC1s-A
   5'amine TTT TTT TTT TTT TTT TTT GCA ATA GGT TTT GAG GGG CAT-3'              (SEQ ID NO:4)
   b.    GC1a-B
   5'amine TTT TTT TTT TTT TTT TTT TTC TGG GCC ACT GAC TGA TTT-3'              (SEQ ID NO:5)

4. Amplitaq DNA Polymerase, Stoffel Fragment (Applied Biosystems)

5. 1 ng/µl genomic DNA samples (Corriell)

6. 10 µm Polysciences COOH functionalized beads 2.5% solids (Polysciences)

7. Hybridization buffer: 6X SSC pH 7.0 (900 mM NaCl), 5X Denhardt's solution, 0.01 M EDTA, 0.5% SDS and 100 mg/ml sheared, denatured salmon sperm DNA (Biowhittaker)

8. Wash buffer: 2X SSC (300 mM NaCl), 0.1% SDS 9. 10 mM PBS pH 7.4 (Sigma)

10. 10 mM PBS/1% BSA 11. 1-[3-(dimethyl-amino)-propyl]-ethylcarbodiimide hydrochloride (EDC; Sigma)

12. Streptavidin Cy-Chrome ® corjugate (BD Pharmingen)

| PCR Protocol |
|---|
| Concentration per 50 µl reaction |
| 1X Amplitaq Stoffel buffer (10 mM Tris-HCl, 10 mM KCl, pH 8.3) |
| 200 µM each dNTP |
| 25 mM MgCl$_2$ |
| 2.5 U Amplitaq Stoffel enzyme |
| 200 nM reverse primer (LDLrab) |
| 100 nM forward primer (LDLrA-GC1s) |
| 100 nM forward primer (LDLrB-GC1a) |
| 1 ng/µl genomic DNA |
| Amplify: |
| 2 cycles of 30 seconds at 94° C., 30 seconds at 62° C., 30 seconds at 72° C.; 36 cycles of 30 seconds at 94° C., 30 seconds at 60° C., and 30 seconds at 72° C.; and 7 minutes at 72° C. |

Conjugation of Oligonucleotides to Beads

80 µl of 10 micron Polysciences beads were spun down per conjugation reaction. (8000 RPM in Eppendorf microcentrifuge for 3 minutes). The supernatant was removed and the beads were resuspended in 100 µl of Imidazole buffer (0.1M, pH 7.0). The beads were spun down again and the supernatant removed. The beads were again washed in Imidazole buffer. After the second wash, the beads were resuspended in 20 µl Imidazole buffer. 2.0 µl of 100 µM oligonucleotide and 100 µl of 200 mM EDC made fresh in Imidazole buffer pH 7.0 were added to the beads. The beads were then incubated for 4 hours at room temperature with shaking. The beads were then spun down, the supernatant removed, and the beads were resuspended in 200 µl of 2×SSC, 0.5% SDS; this step was then repeated. The beads were then again spun down, the supernatant was removed and the beads were resuspended in 100 µl of water; this step was also repeated. The beads were then spun down, the supernatant removed and the beads were resuspended in 45 µl of PBS pH 7.4.

Hybridization of Amplicon to Generic Oligo Conjugated Beads

5 µl of heat denatured amplicon were added to 2.5 µl of conjugated beads in 85 µl of hybridization buffer and incubated at 45° C. for 15 minutes. The beads were spun down, the supernatant removed and the beads were then resuspended in 100 µl 1.5×SSPE (225 MM NaCl), 0.1% SDS. The beads were again spun down and the supernatant removed to wash away excess amplicon. The beads were then resuspended in 50 µl of PBS/BSA. 0.5 µl of 0.2 mg/ml in Streptavidin-Cy-Chrome® dye was added and incubated with the beads for 1 hour at room temperature. The beads were then spun down and resuspended in 400 µl PBS pH 7.4. The beads were analyzed on flow cytometer in PBS pH 7.4.

Figure 15:
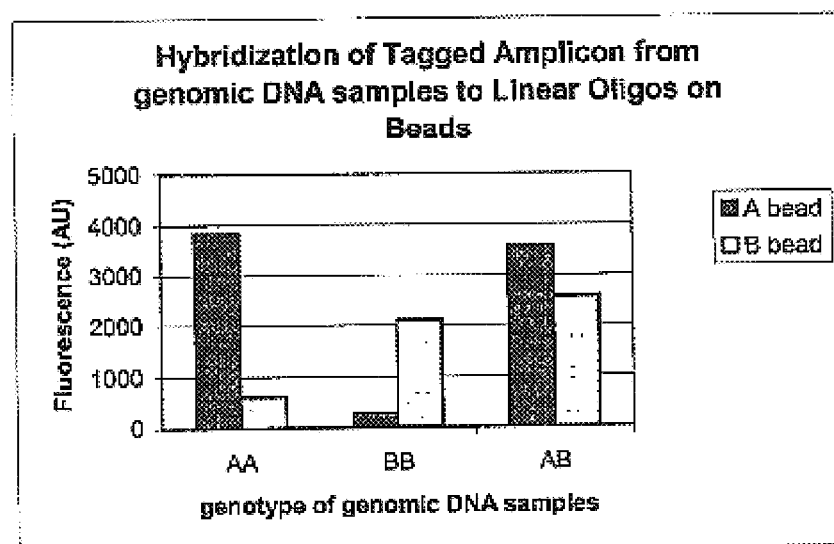
FIG. 15 is a pictorial illustration of the results of hybridization of amplicons produced from two alleles of the LDL receptor by PCR amplification of wildtype (AA), mutant (BB), and in heterozygous (AB) genomic DNA samples to generic capture probe oligonucleotide-conjugated beads. The solid bars are the results obtained with beads comprising the A complementary oligonucleotide and the stippled bars are the results obtained with beads comprising the B complementary oligonucleotide.

The unique capture sequence-tagged amplicon showed sequence-specific hybridization to its complement attached to beads as seen in FIG. 15. Both alleles present in the heterozygous sample could be independently amplified and identified, and heterozygous samples could be distinguished from homozygous samples.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A method for assaying for an amplification product from a first target polynucleotide, comprising:

providing a sample that is suspected of containing the amplification product, wherein the amplification product is a polynucleotide comprising a first label and a capture sequence not present in the target polynucleotide at the same position, wherein the first label is a semiconductor nanocrystal, wherein the amplification product is formed by primer extension from a template and is produced by a process comprising incorporating the polynucleotide comprising the first label into the amplification product using a polymerase, wherein said template comprises a complement to the target polynucleotide and a target noncomplementary region, wherein said capture sequence is a complement to said target noncomplementary region;

providing a substrate that is conjugated to a first capture probe;

contacting the sample with the capture probe under a first set of hybridization conditions;

wherein the capture probe is a polynucleotide that can bind to the capture sequence under said first set of hybridization conditions; and determining if the first label is associated with the substrate.

2. The method of claim 1, wherein the substrate is selected from the group consisting of a microsphere, a chip, a slide, a multiwell plate, a membrane, an optical fiber, and a porous gel matrix.

3. The method of claim 1, wherein the substrate is a slide.

4. The method of claim 1, wherein the substrate is conjugated to a plurality of different capture probe polynucleotides having corresponding different sequences, wherein each of said different capture probes can selectively bind to a corresponding different capture sequence on a corresponding different amplification product.

5. The method of claim 2, wherein the substrate is a first microsphere comprising a first spectral code comprising a first semiconductor nanocrystal and first fluorescence characteristics.

6. The method of claim 5, wherein the first semiconductor nanocrystal comprises a core selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, AlAs, AlP, AlSb, AlS, Ge, Si, Pb, PbS, PbSe, an alloy thereof, and a mixture thereof.

7. The method of claim 5, wherein the core is CdSe.

8. The method of claim 5, wherein the first semiconductor nanocrystal comprises a shell.

9. The method of claim 8, wherein the shell is ZnS.

10. The method of claim 1, wherein the semiconductor nanocrystal comprises a core selected from the group consisting of ZnS, ZnSe, ZnTe, CdS, CdSe, CdTe, HgS, HgSe, HgTe, MgSt MgSe, MgTe, CaS, CaSe, CaTe, SrS, SrSe, SrTe, BaS, BaSe, BaTe, GaN, GaP, GaAs, GaSb, InN, InP, hnAs, InSb, AlAs, AlP, AlSb, AlS, Ge, Si, Pb, PbS, PbSe, an alloy thereof, and a mixture thereof.

11. The method of claim 10, wherein the core is CdSe.

12. The method of claim 1, wherein the semiconductor nanocrystal comprises a shell.

13. The method of claim 12, wherein the shell is ZnS.

14. The method of claim 1, wherein the sample is assayed for the presence of the amplification product.

15. The method of claim 1, wherein the sample is assayed to determine the amount of the amplification product.

16. The method of claim 15, wherein the amplification product is produced at a detectably higher level from at least one allele of a locus having at least two alleles.

17. The method of claim 5, wherein the sample is suspected of containing a second amplification product from a second target polynucleotide and is further contacted under a second set of hybridization conditions with a second capture probe conjugated to a microsphere, wherein the second capture probe is a polynucleotide, wherein the microsphere can be the first microsphere or a different second microsphere, wherein when the microsphere is a different second microsphere it comprises a second spectral code comprising second fluorescence characteristics, said second spectral code distinguishable from the first spectral code, wherein the second set of hybridization conditions can be the same as or different than the first set of hybridization conditions, wherein the second capture probe can hybridize to the second amplification product under the second set of hybridization conditions, wherein the second amplification product comprises a second label, which can be the first label when the microsphere is a different second microsphere or can be a different second label, and determining if the second label is associated with the microsphere.

18. The method of claim 17, wherein the sample is suspected of containing a third amplification product from a third target polynucleotide and is further contacted under a third set of hybridization conditions with a third capture probe conjugated to a microsphere, wherein the third capture probe is a polynucleotide, wherein the microsphere can be the first microsphere, the second microsphere or a different third microsphere, wherein when the microsphere is a different third microsphere it comprises a third spectral code comprising third fluorescence characteristics, said third spectral code distinguishable from the first spectral code and the second spectral code, wherein the third set of hybridization conditions can be the first set of hybridization conditions, the second set of hybridization conditions, or a different third set of hybridization conditions, wherein the third capture probe can hybridize to the third amplification product under the third set of hybridization conditions, wherein the third amplification product comprises a third label, which can be the first label or the second label when the microsphere is a different third microsphere or can be a different third label, and determining if the third label is associated with the microsphere.

19. The method of claim 18, wherein the sample is suspected of containing a fourth amplification product from a fourth target polynucleotide and is further contacted under a fourth set of hybridization conditions with a fourth capture probe conjugated to a microsphere, wherein the fourth capture probe is a polynucleotide, wherein the microsphere can be the first microsphere, the second microsphere, the third microsphere or a different fourth microsphere, wherein when the microsphere is a different fourth microsphere it comprises a fourth spectral code comprising fourth fluorescence characteristics, said fourth spectral code distinguishable from the first spectral code, the second spectral code and the third spectral code, wherein the fourth set of hybridization conditions can be the first set of hybridization conditions, the second set of hybridization conditions, the third set of hybridization conditions or a different fourth set of hybridization conditions, wherein the fourth capture probe can hybridize to the fourth amplification product under the fourth set of hybridization conditions, wherein the fourth amplification product comprises a fourth label, which can be the first label, the second label or the third label when the microsphere is a different fourth microsphere or can be a different fourth label, and determining if the fourth label is associated with the microsphere.

20. The method of claim 17, wherein the first and second amplification products are produced from a single locus.

21. The method of claim 20, wherein the first and second amplification products differ by a single nucleotide.

22. The method of claim 17, wherein the second microsphere is the first microsphere and both first and second capture probes are conjugated to the first microsphere, and wherein the first and second labels are fluorophores comprising distinguishable fluorescence characteristics.

23. The method of claim 17, wherein the second microsphere is a different second microsphere, and wherein the first and second labels each comprise the same fluorophore.

24. The method of claim 17, wherein the second microsphere is a different second microsphere, and wherein the first and second labels respectively comprise first and second fluorophores having distinguishable fluorescence characteristics.

25. The method of claim 1, wherein the substrate is further conjugated to a second capture probe, wherein the second capture probe can preferentially bind to a second capture sequence on a second amplification product, said second amplification product comprising a second label that can be the same as or different than the first label, wherein the binding of the first amplification product to the first capture probe and of the second amplification product to the second capture probe can be independently determined.

26. The method of claim 25, wherein the substrate is further conjugated to a third capture probe, wherein the third capture probe can preferentially bind to a third capture sequence on a third amplification product, said third amplification product comprising a third label that can be the same as or different than the first label and/or the second label, wherein the binding of the third amplification product to the third capture probe can be independently determined.

27. The method of claim 26, wherein the substrate is further conjugated to a fourth capture probe, wherein the fourth capture probe can preferentially bind to a fourth capture sequence on a fourth amplification product, said fourth amplification product comprising a fourth label that can be the same as or different than the first label and/or the second label and/or the third label, wherein the binding the fourth amplification product to the fourth capture probe can be independently determined.

28. The method of claim 25, wherein the first and second capture probes are conjugated to first and second positions on the substrate, and wherein the binding of the first amplification product to the first capture probe and of the second amplification product to the second capture probe can be independently determined by determining if the first label is associated with the first position and if the second label is associated with the second position.

29. The method of claim 25, wherein the second label is different from the first label, and wherein the binding of the first amplification product to the first capture probe and of the second amplification product to the second capture probe can be independently determined by determining if the first label is associated with the substrate and if the second label is associated with the substrate.

* * * * *